(12) United States Patent
Fierkens et al.

(10) Patent No.: US 8,454,559 B2
(45) Date of Patent: Jun. 4, 2013

(54) HYPODERMIC SYRINGE WITH RETRACTABLE NEEDLE

(75) Inventors: Richardus Gerardus Theodora Fierkens, 'S-Heerenberg (NL); Richardus Henricus Johannes Fierkens, Herwen (NL); Arnoldus Theodorus Maria Telkamp, Velp (NL); Dirk Vogelaar, Zoetermeer (NL)

(73) Assignee: Addino B.V., Zoetermeer (NL)

( * ) Notice: Subject to any disclaimer, the term of this patent is extended or adjusted under 35 U.S.C. 154(b) by 88 days.

(21) Appl. No.: 12/999,853

(22) PCT Filed: Jun. 19, 2009

(86) PCT No.: PCT/NL2009/050362
§ 371 (c)(1),
(2), (4) Date: Mar. 8, 2011

(87) PCT Pub. No.: WO2009/154462
PCT Pub. Date: Dec. 23, 2009

(65) Prior Publication Data
US 2011/0264041 A1   Oct. 27, 2011

Related U.S. Application Data

(60) Provisional application No. 61/073,901, filed on Jun. 19, 2008.

(30) Foreign Application Priority Data

Jun. 19, 2008  (NL) .................................. 2001702

(51) Int. Cl.
*A61M 5/50* (2006.01)
(52) U.S. Cl.
USPC ................ 604/110; 604/90; 604/91; 604/195

(58) Field of Classification Search
USPC ............ 604/90, 91, 110, 111, 194, 195, 207, 604/218, 221, 236, 237, 247, 256
See application file for complete search history.

(56) References Cited

U.S. PATENT DOCUMENTS 5,738,655 A * 4/1998 Vallelunga et al. ........... 604/110
6,117,112 A * 9/2000 Mahurkar ..................... 604/194
(Continued)

FOREIGN PATENT DOCUMENTS

| FR | 2 718 358 A | 10/1995 |
| WO | 96/32977 A | 10/1996 |
| WO | 03/066144 A | 8/2003 |

*Primary Examiner* — Nicholas Lucchesi
*Assistant Examiner* — Gerald Landry, II
(74) *Attorney, Agent, or Firm* — Ladas & Parry LLP

(57) ABSTRACT

Hypodermic syringe having a barrel which with an inner wall thereof defines a reservoir, a closing-off device near the first end of the barrel, and a plunger that is movably placed in the second end of the barrel, wherein the closing-off device comprises a circumferential wall that sealingly abuts the inner wall of the barrel, at the side facing away from the nozzle is provided with a recess extending along a centre line of the closing-off device and over the full width thereof, which recess merges into the through-opening, with in the recess two diametrically opposite flexible locking members, extending in the longitudinal direction of the recess and towards the inner wall, which locking members engage into diametrically placed locking grooves in the inner wall, and at the side facing away from the nozzle, at a circumferential part of the closing-off device situated outside of the recess, is provided with two diametrically opposite and radially outwardly extending blocking members, that engage in diametrically placed blocking grooves in the inner wall.

29 Claims, 22 Drawing Sheets

U.S. PATENT DOCUMENTS

| | | | |
|---|---|---|---|
| 2003/0093038 A1* | 5/2003 | Chiang | 604/240 |
| 2004/0024366 A1* | 2/2004 | Tsai | 604/197 |
| 2005/0020984 A1* | 1/2005 | Lesch | 604/187 |
| 2005/0027250 A1* | 2/2005 | Suresh et al. | 604/110 |
| 2005/0148931 A1* | 7/2005 | Juhasz | 604/110 |
| 2006/0106342 A1* | 5/2006 | Cox | 604/110 |
| 2006/0106343 A1* | 5/2006 | Alchas et al. | 604/110 |
| 2006/0173411 A1* | 8/2006 | Barere | 604/110 |
| 2008/0215000 A1* | 9/2008 | Barere | 604/110 |
| 2011/0015572 A1* | 1/2011 | Thorley et al. | 604/110 |
| 2011/0178501 A1* | 7/2011 | Cleathero | 604/506 |

\* cited by examiner

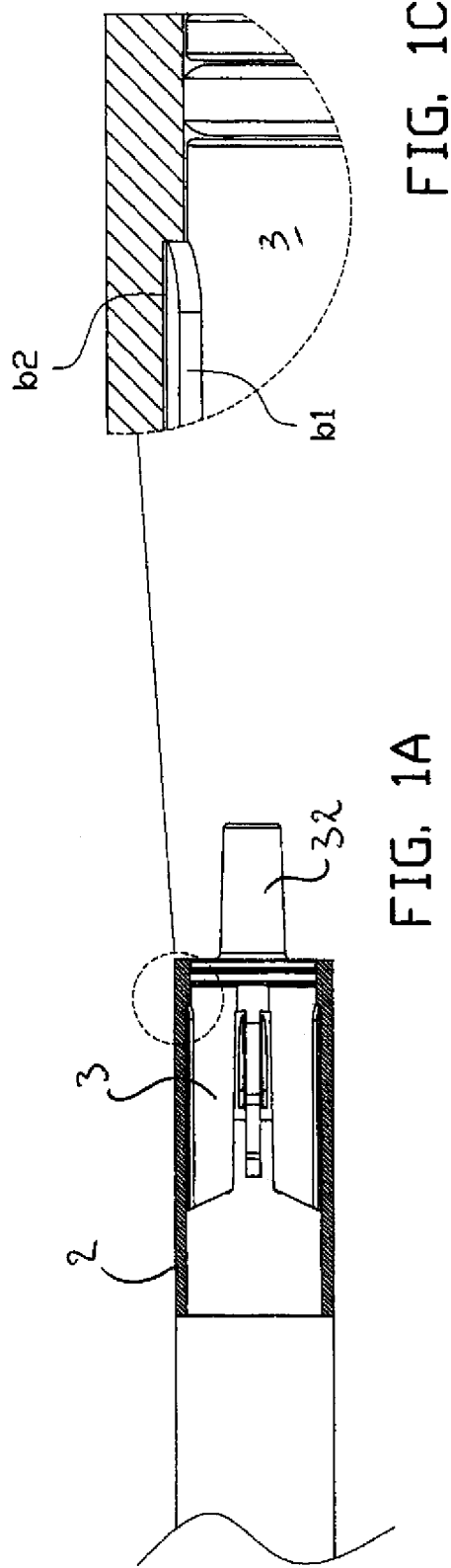
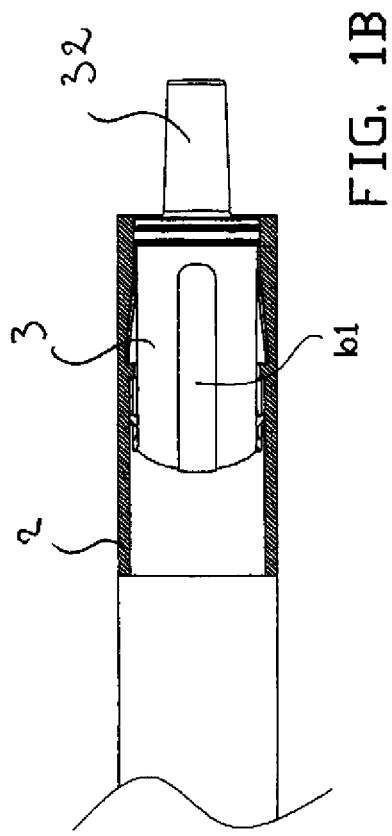
FIG. 1A
FIG. 1B
FIG. 1C

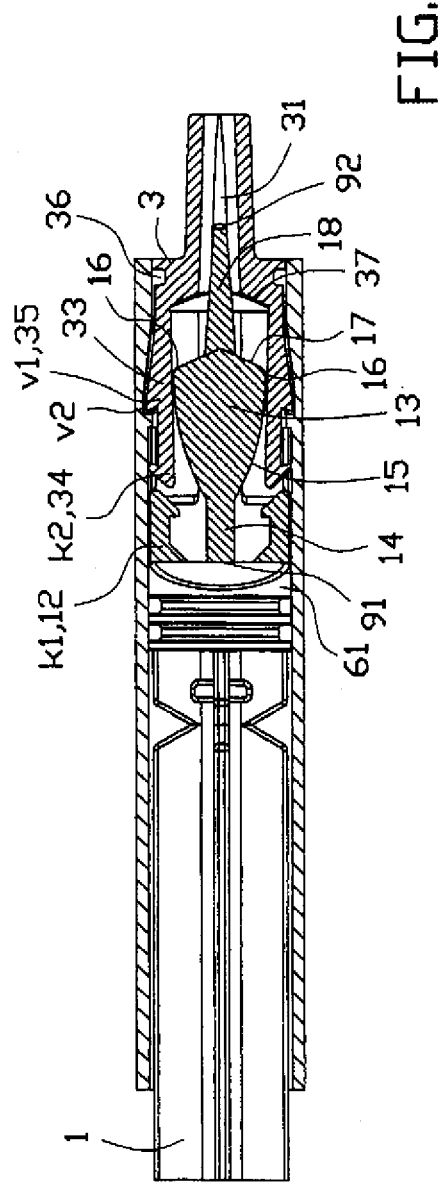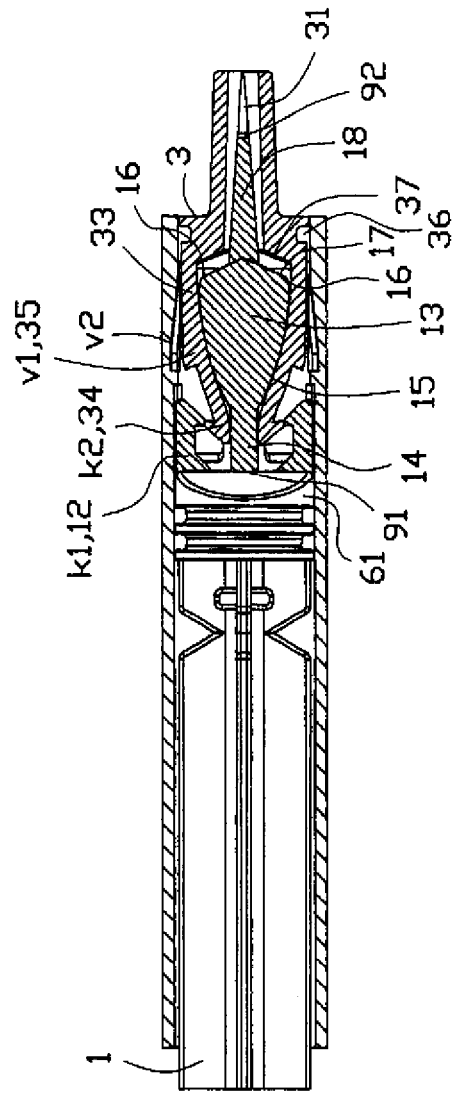

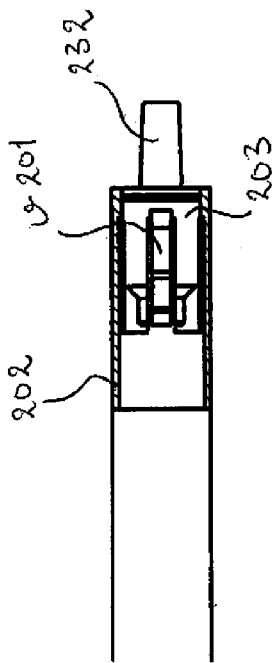
FIG. 18A
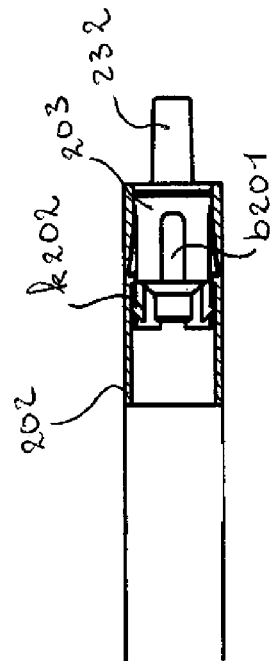
FIG. 18B
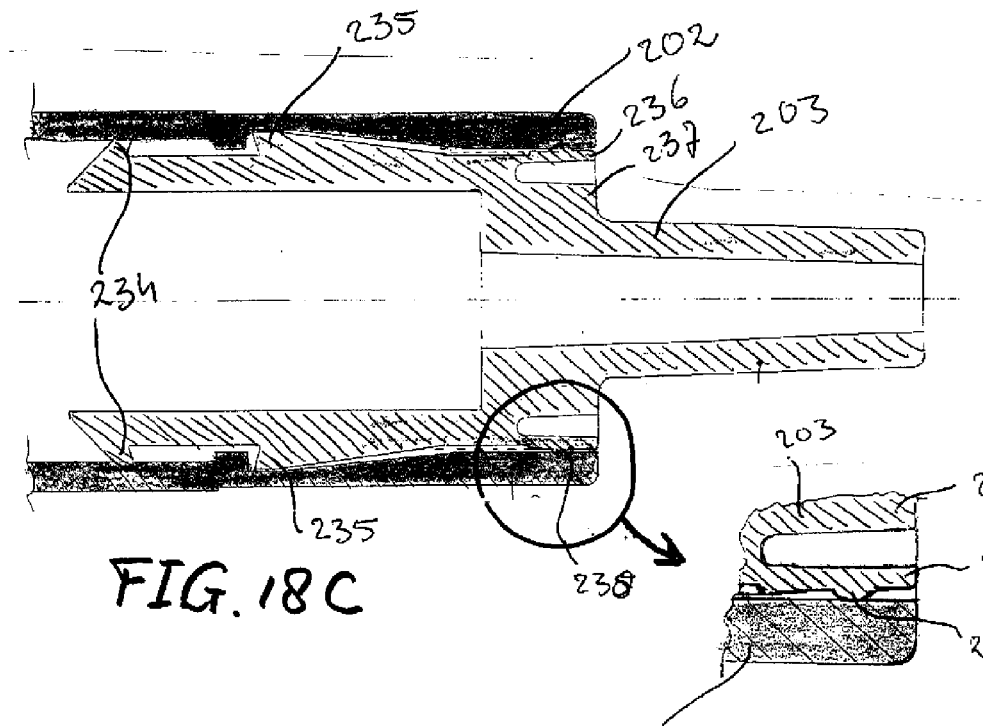
FIG. 18C
FIG. 18D

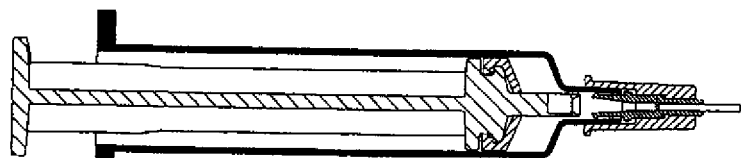
Workingstep 1
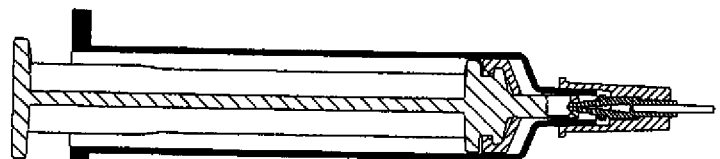
Workingstep 2
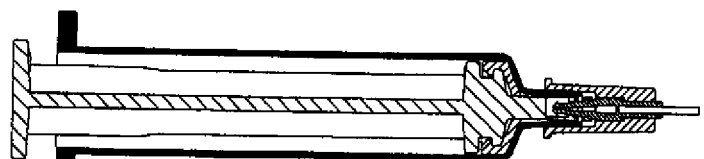
Workingstep 3
Workingstep 4
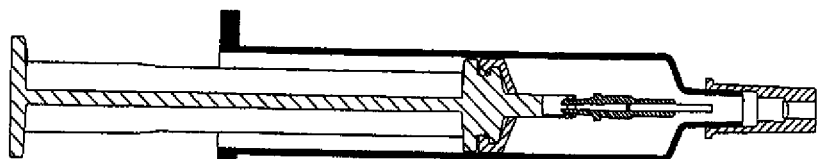
Workingstep 5
FIG.31

US 8,454,559 B2

HYPODERMIC SYRINGE WITH RETRACTABLE NEEDLE

This application is a 371 of PCT/NL09/50362 filed on Jun. 19, 2009 and claims priority from provisional application 61/073901 filed on Jun. 19, 2008, the contents of which are incorporated herein by reference.

BACKGROUND OF THE INVENTION

The invention relates to a hypodermic syringe comprising:
a barrel which with an inner wall thereof defines a reservoir, comprising a first section near a first end of the barrel and a second section near a second end of the barrel,
a closing-off device, placed in the first section of the barrel, for closing off the first end of the barrel, wherein the closing-off device is provided with a through-opening outwardly debouching in a nozzle adapted for a coupling to a needle device, and
a plunger, slidably placed in the second section of the barrel, for pushing a fluid out of the barrel at penetration into the barrel, wherein the plunger at least partially protrudes out of the barrel at the second end thereof, and wherein a first end of the plunger is inserted in the barrel and comprises first coupling members.

Such conventional hypodermic syringes, particularly their nozzles, are standardised wherein various different needles can be placed on the nozzle. A drawback of said hypodermic syringes is however that the needle cannot be retracted into the barrel. For a retractable needle the construction of the hypodermic syringe needs to be drastically adapted.

STATE OF THE ART

In the course of time many different hypodermic syringes have been developed for retracting the nozzle with the needle placed thereon into the barrel of the syringe.

In WO 96/32977 a hypodermic syringe is described comprising a barrel, a plunger and a needle mount that can be retracted into the barrel. The needle mount is secured to a first open end of the barrel by means of flexible arms provided with shoulders that cooperate with shoulders formed in recesses of the barrel wall by placing an extra annular body placed at a second diameter step in the barrel. Furthermore the first open end of the barrel is provided with a diameter step in the barrel for having the needle mount rest thereon. Thus the needle mount is confined between the second diameter step in the barrel and the extra annular body. At an end surface the plunger is provided with slots able to receive the distal ends of the flexible arms. The slots have surfaces that act on the arms for disengaging the arms from the recesses and catches that cooperate with the closure hooks on the flexible arms so that the needle mount is retracted by the plunger. A drawback of this hypodermic syringe is that both the barrel and the plunger have to be composed from a large number of separate parts. Particularly placing and attaching the annular body at the diameter step in the barrel is a laborious step.

A comparable construction is known from US 2003/0093038. In said hypodermic syringe the arms are designed to be cylinder wall members that are placed around the periphery of the needle mount and which rest against small cams placed on the inner wall of the barrel and extending into the barrel. Comparable cams are also placed near a first open end of the barrel for confining the needle mount within the barrel. A drawback of said hypodermic syringe is that, also due to the cams, it is difficult to injection mould the barrel. When removing the barrel from the injection mould the cams are quite often damaged which results in not obtaining a proper confinement of the needle mount. Furthermore the needle mount and plunger are difficult to injection mould due to their specific shape. Finally said hypodermic syringe has a relatively large dead space in the needle mount.

It is an object of the present invention to provide an alternative embodiment of a hypodermic syringe with retractable needle mount on which standard needles can be placed that are retractable into the barrel, and which can be manufactured in a simple way using a minimum number of parts.

SUMMARY OF THE INVENTION

The object of the invention is achieved with a hypodermic syringe according to the preamble, wherein the closing-off device comprises a circumferential wall that sealingly abuts the inner wall of the first section of the barrel,
wherein the closing-off device at the side facing away from the nozzle is provided with a recess extending along a centre line of the closing-off device and over the full width of the closing-off device, which recess in the direction of the nozzle merges into the trough-opening, wherein in the recess two diametrically opposite flexible first locking members are placed that extend in the longitudinal direction of the recess and towards the circumferential wall, which locking members by engaging into diametrically placed locking grooves in the inner wall lock the closing-off device against a movement in the direction from the first end to the second end, wherein the locking members at or near their end facing away from the nozzle comprise second coupling members for coupling to the first coupling members,
wherein the closing-off device at the side facing away from the nozzle, at a circumferential part of the closing-off device that is situated outside of the recess, is provided with two diametrically opposite blocking members that extend substantially parallel to the centre line of the closing-off device and extend radially outward, which blocking members by engaging into diametrically placed blocking grooves in the inner wall lock the closing-off device against a movement in the direction from the second end to the first end.

By using both diametrically placed locking grooves in the inner wall of the barrel for locking against a movement in the direction towards the second end of the barrel, and using diametrically placed blocking grooves in the inner wall of the barrel for blocking against a movement in the direction towards the first end of the barrel, wherein the locking grooves and the blocking grooves do not overlap each other, the barrel can be made by means of a simple injection moulding method.

In one embodiment the locking members and the locking grooves form a form closure in the direction towards the second end, and the blocking members and the blocking grooves form a form closure in the direction towards the first end. One embodiment of such a form closure is a snap engagement of blocking or locking members into the respective grooves. Another embodiment is a locking member having an abutment edge or shoulder facing the second end and a locking groove having an abutment edge or shoulder facing the first end. Another embodiment is a blocking member having an abutment edge or shoulder facing the first end and a blocking groove having an abutment edge or shoulder facing the second end.

In one embodiment the locking members and the locking grooves form a force closure in the direction towards the first end. One embodiment of such a force closure is a locking member having an incline facing the first end and which is at an acute angle to the centre line of the syringe and a locking groove having a corresponding incline. Said design makes it possible to take out a core part of the injection mould shaping the inside of the barrel of or near the locking grooves, out of the barrel via the first end of the barrel, wherein the barrel temporarily deforms substantially without damages.

In one embodiment the first section of the barrel at a side thereof that faces away from the first end is bounded by a circumferential edge, wherein the first section has a smaller inner diameter than a part of the barrel situated beyond the edge, wherein the blocking groove is formed in said first section and debouches in the edge. In one embodiment the bottom surface of the blocking groove is placed at substantially the same distance to the centre line of the barrel as the part of the barrel situated beyond the edge. This design makes it possible to slide a core part of the injection mould shaping the inside of the barrel of or near the blocking grooves, out of the barrel via the second end of the barrel, without damages.

In one embodiment the locking grooves and the blocking grooves are placed substantially at a same circumference at the inner side of the barrel. In one embodiment a first plane through the centre lines of the blocking grooves is placed substantially perpendicular to a second plane through the centre lines of the locking grooves. In one embodiment an intersecting line between said first and second plane coincides with the centre line of the hypodermic syringe.

In order to retract the closing-off device including the needle device, the end of the plunger is provided with first coupling members and the closing-off device is provided with second coupling members that cooperate with the first coupling means. In that way the plunger can be coupled to the closing-off device for retracting the assembly comprising the plunger or piston, closing-off device and needle device into the barrel. In one embodiment the first and second coupling members are adapted for unlocking the locking of the locking members out of the locking grooves. By unlocking the locking members freedom is created for the closing-off device to be moved into the barrel. By unlocking the closing-off device during effecting the coupling to the plunger or piston, the closing-off device is taken along in case of a pulling motion at the plunger.

In one embodiment of said hypodermic syringe the inner wall of the first section of the barrel is substantially cylindrical or has an increasing diameter course in a direction from the first end towards the second end of the barrel. The designs in the first section of the barrel thus described are part of embodiments having the releasing condition for the closing-off device.

In one embodiment of said closing-off device the dimensions of the nozzle are adapted for a coupling to a needle or needle device suitable or intended for standard hypodermic syringes, meaning hypodermic syringes without retraction device. As a result the standard needle or needle device can be stored in the barrel after use by retracting the closing-off device. By providing the closing-off device with a nozzle on which standard conventional needles can be placed, organisations are able to limit the purchase of needles to said standard conventional needles, and substantially limit the purchase of hypodermic syringes to hypodermic syringes according to the invention. Due to the standard nozzle the hypodermic syringes according to the invention can also be coupled to other devices, such as a drip.

In one embodiment the closing-off device comprises a first end near the first end of the barrel, wherein the diameter of said first end exceeds a diameter of the standard needle device. As a result the part of the needle device having the largest diameter measured transverse to the longitudinal direction of the needle device also fits through the first end of the barrel.

In one embodiment the diameter of the closing-off device at the first end exceeds 6 mm, preferably exceeds 8 mm. Diameters of such dimensions are commonly used and as a result a hypodermic syringe with retractable needle device is provided on which all needles having dimensions according to the standard in organisations can be used.

In one embodiment an inner diameter of the second section of the barrel, comprising a substantially cylindrical inner wall, exceeds or equals an outer diameter of the closing-off device. In that way the part of the closing-off device having the largest diameter measured transverse to the longitudinal direction of the closing-off device also fits through the second end of the barrel.

In one embodiment the shape of the end of the plunger that is inserted in the barrel in the condition of deepest penetration substantially fits close to the shape of the end of the closing-off device present in the barrel. In this way the volume taken up by the fluid is filled by the volume of the plunger, as a result of which the residual volume of the fluid left in the barrel after injection remains limited to a minimum.

In one embodiment the plunger is provided with a filler body that at least partially fills the through-opening. In this way also the fluid in the nozzle is at least partially pushed out of there.

In one embodiment the hypodermic syringe comprises a stop mechanism adapted for blocking a movement of the plunger in the direction of the first end of the barrel, wherein the stop mechanism in a first position bounds the plunger that is to penetrate the barrel so that the first end of the plunger does not couple itself to the closing-off device, and wherein the stop mechanism in a second position allows the plunger that is to penetrate the barrel to couple to the closing-off device. For sucking up fluid it is necessary to insert the plunger as deeply as possible into the barrel. If, however, the plunger would already couple at this point, the closing-off device would also be pulled along when retracting the plunger. In order to prevent this the stop mechanism in the first position bounds the movement of the plunger such that the coupling means of the plunger and the closing-off device do not effect a coupling.

For housing the needle in the barrel it is indeed necessary that the coupling means of the plunger and the closing-off device form a coupling. For that purpose the stop mechanism needs to be brought into its second position which ensures that the plunger is able to get deeper into the barrel so that the coupling is effected.

In one embodiment thereof the stop mechanism in the second position blocks the assembly comprising the plunger and the closing-off device against said assembly thrusting through in the direction of the first end of the barrel. When the closing-off device as a result of a firm pressing force is pushed slightly out of the barrel it will be difficult to push the closing-off device back inside again, which for that matter also entails the risk of the needle inadvertently pricking someone's skin. When the stop mechanism is in its second position it is prevented that the closing-off device can be pushed out of the barrel.

In one embodiment the stop mechanism is arranged near the second end of the plunger. In this way it has turned out to be possible to realise a simple construction that makes an easily accessible operation possible.

In one embodiment the barrel comprises a guiding device for guiding the plunger. In one embodiment the guiding device, at least an end thereof, engages onto the plunger for fixating the orientation of the plunger around the centre line of the hypodermic syringe.

In one embodiment the guiding device comprises first connecting means, and the barrel comprises second connecting means cooperating with the first connecting means, wherein the first and second connecting means are adapted for a connection of the guiding device to the barrel. When assembling the hypodermic syringe in the factory, first the closing-off device and the plunger are introduced into the barrel. The guiding device can be placed in a first condition wherein the guiding device leaves the opening at the second end of the barrel completely free, and in a second condition wherein the guiding device is partially inserted into the opening at the second end of the barrel and engages onto the plunger for its rotation-fixed guidance. In order to have the first and second coupling means couple adequately, a fixed orientation of the plunger with respect to the closing-off device may be desirable. The same goes for having the first locking members unlock. As soon as the plunger has been sufficiently placed and oriented in the barrel, the connecting means of the guiding device in their second condition can be connected to the connecting means of the barrel.

In one embodiment the plunger comprises a rib extending in the longitudinal direction of the plunger, and the guiding device comprises an end comprising protruding parts for at least partially embracing the rib, in whatever inserted position the plunger may be. In this way a rib is continuously guided by a guiding device when pushing in and retracting the plunger.

In one embodiment the plunger comprises movement limitation means for checking the guiding device on the barrel, which means bound a movement of the plunger in the direction of the second end of the barrel. In that way the position of the plunger with respect to the barrel is defined, wherein the plunger can be broken off.

In one embodiment the plunger is constructed with a weakening for breaking and splitting the plunger, wherein the weakening is placed particularly near the end of the plunger present in the barrel. The plunger can be split from the retracted assembly when the weakening is placed just outside of the barrel. The length of the hypodermic syringe is thus roughly halved. Quite apart from the fact that waste is processed more efficiently, splitting removes the risk of the needle being accidentally pushed out of the barrel again.

In one embodiment the second section of the barrel, comprising a substantially cylindrical inner wall, has a cross-sectional surface exceeding or equaling a cross-sectional surface of the first section of the barrel. In that way the volume in the second section for injecting or sucking up larger quantities of fluid can be obtained. Moreover it becomes possible to use an identical closing-off device in hypodermic syringes independent of the thickness of the hypodermic syringe. For instance the second section of the barrel of a hypodermic syringe for administering for instance 3 cc of fluid can have the same inner diameter over its full length. In case of a barrel of a hypodermic syringe for administering larger volumes the second section of the inner diameter of the barrel can be designed with a desired girth.

In one embodiment the plunger is provided with a filler body that at least partially fills the recess and the through-opening in the closing-off device. In that way the volume taken up by the fluid is filled by the volume of the plunger, as a result of which the residual volume of the fluid left in the barrel after injection remains limited to a minimum. As the plunger is provided with a filler body that at least partially fills the through-opening, also the fluid in the nozzle is at least partially pushed out of there.

In one embodiment the closing-off device at an end situated near the first end of the barrel is provided with a rib running around the closing-off device and extending radially outward, wherein the rib is integrally formed with the closing-off device. Said rib ensures an adequate sealing between the closing-off device and the inner wall of the barrel.

The aspects and measures described in this description and the claims of the application and/or shown in the drawings of this application may where possible also be used individually. Said individual aspects, such as the filler body at the end of the plunger with which the residual volume of the fluid left in the barrel after injection remains limited to a minimum, and other aspects may be the subject of divisional patent applications relating thereto. This particularly applies to the measures and aspects that are described per se in the sub claims.

SHORT DESCRIPTION OF THE DRAWINGS

The invention will be elucidated on the basis of a number of exemplary embodiments shown in the attached drawings, in which:

FIG. 1A shows a first side view of the barrel in which the closing-off device is situated in locked condition;

FIG. 1B shows a second side view of the barrel in which the closing-off device is situated in locked condition;

FIG. 1C shows a detail of the blocking members with which the closing-off device is blocked in the barrel;

FIG. 2 shows a cross-section of the hypodermic syringe of FIG. 1 in which the plunger is situated in a position in which a coupling to the closing-off device just has not been effected yet, and wherein the sucking up of fluid could be carried out;

FIG. 3 shows a cross-section of the hypodermic syringe of FIG. 1 in which the closing-off device is unlocked from the barrel;

FIG. 18A shows a first side view of the barrel in which the closing-off device is situated in locked condition;

FIG. 18B shows a second side view of the barrel in which the closing-off device is situated in locked condition;

FIG. 18C shows a view in cross-section of the barrel with closing-off device;

FIG. 18D shows a detail of FIG. 18C;

FIG. 31 shows a view in cross-section of the syringe of FIG. 21, with the plunger at different process steps within the syringe barrel.

DETAILED DESCRIPTION OF THE DRAWINGS

Figure 1:
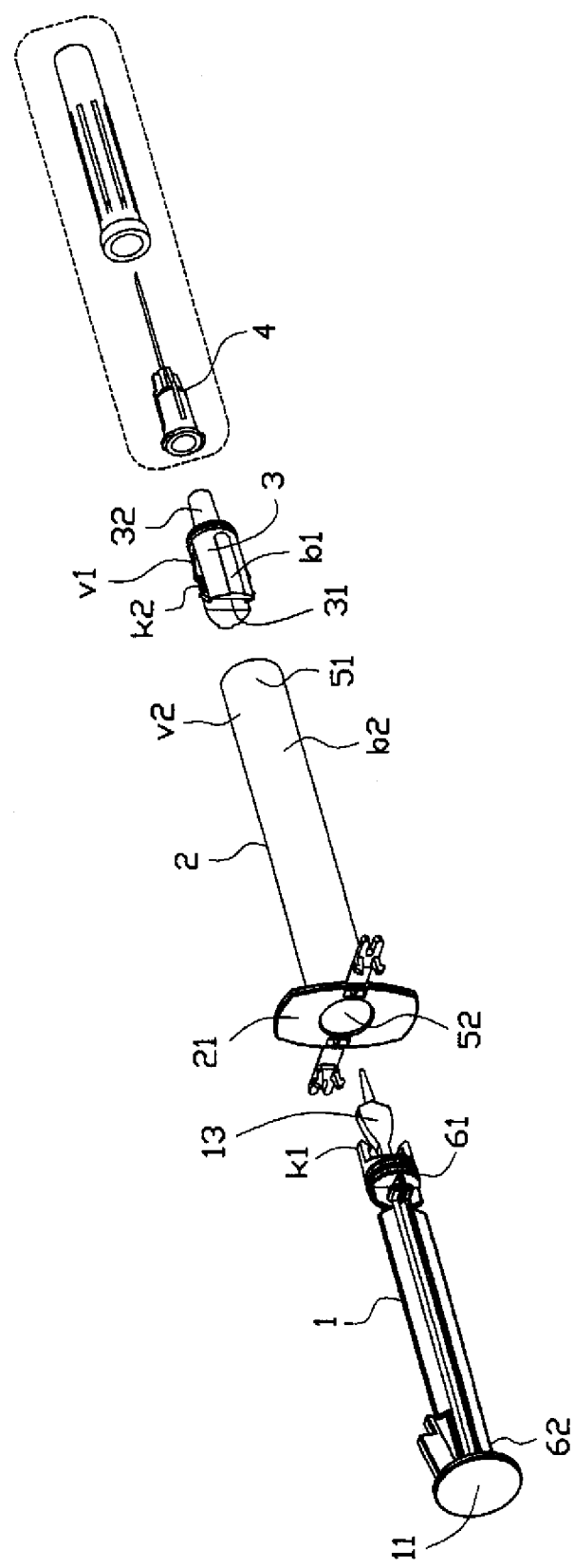
FIG. 1 shows a view in perspective of a first exemplary embodiment of the hypodermic syringe in a disassembled condition.

Below a number of exemplary embodiments of the present invention will be described while referring to the drawings.

FIG. 1 is a disassembled view in perspective of the hypodermic syringe and shows plunger 1 (also called piston), barrel 2 (also called reservoir or housing), closing-off device 3 (also called needle mount or anchor), and needle device 4.

The barrel 2 has a substantially cylindrical inner wall, and comprises a flange 21 at a second end 52 for holding the hypodermic syringe and a first end 51 facing away from the second end of the barrel.

The closing-off device 3 is adapted for closing off the first end 51 of the barrel 2, wherein the closing-off device 3 is provided with a through-opening 31 that outwardly debouches into a nozzle 32 that is adapted for coupling to a needle device 4. The closing-off device 3 comprises second coupling means k2 at a side facing away from the nozzle 32.

The plunger 1 can movably be placed in the barrel 2 for pushing a fluid out of the barrel at penetration into the barrel 2, wherein the plunger 1 at least partially protrudes out of the barrel 2 at the second end 52 thereof. The first end 61 of the plunger 1 is inserted in the barrel 2. The second end 62 of the plunger facing away from the first end 61 comprises a pressing part 11. The first end 61 of the plunger comprises first coupling means k1 cooperating with the second coupling means k2, wherein first coupling means k1 and second coupling means k2 are adapted for a coupling of the plunger 1 to the closing-off device 3 in order to move the assembly of the plunger 1 and the closing-off device 3 in the barrel 2 in the direction of the second end 52 of the barrel 2.

The closing-off device 3 is in this case movable in the barrel 2, such that the closing-off device 3 optionally including a needle device 4, is retractable into the barrel 2, wherein the circumferential wall of the closing-off device 3 sealingly abuts the inner wall of the barrel 2, at least at the first end 51 of the barrel 2.

The closing-off device 3 is provided with a nozzle 32 wherein the dimensions of the nozzle 32 are adapted for a coupling to a standard needle or needle device 4 that is commonly suitable or intended for hypodermic syringes without retraction device.

The closing-off device 3 is primarily intended for closing off the barrel 2 at its first end 51. Subsequently the closing-off device 3 that is movable in the barrel 2 comprises the following characteristics:

The closing-off device 3 is adapted for coupling to the plunger 1 in order to be retracted into the barrel as an assembly.

The closing-off device 3 is adapted for not being pushed out of the barrel 2 during displacing the fluid. For that purpose the closing-off device 3 comprises first blocking members b1 and the inner wall of the barrel 2 at the first end 51 thereof second blocking members, particularly blocking groove b2 (see FIGS. 1A, 1B and 1C) cooperating with the first blocking members b1, wherein the first blocking members b1 and the second blocking members b2 are adapted for blocking a movement of the closing-off device 3 in the direction of the first end 51 of the barrel (to the outside).

The closing-off device 3 is adapted for being rotation-fixedly placed in the barrel 2 at the first end of the barrel 2. In that case the same blocking members b1 and b2 can be used wherein they are adapted for blocking a rotation of the closing-off device 3 about its centre line.

The closing-off device 3 is adapted for not being pushed into the barrel 2 during insertion of the needle into an object (not shown). For that purpose the closing-off device 3 comprises first locking members v1 and the inner wall of the barrel 2 near its first end 51 second locking members, particularly locking groove v2 (see FIGS. 2, 3, 4 and 5) cooperating with the first locking members v1, wherein the first locking members v1 and the second locking members v2 are adapted for a locking of a movement of the closing-off device 3 in the direction of the second end 52 of the barrel (to the inside).

On the one hand the closing-off device 3 is adapted for not moving inside in the barrel 2 during insertion of the needle into an object. For that purpose the locking members v1 form a form closed connection with locking members v2 resulting in a locking.

On the other hand the closing-off device 3, after the needle has been inserted into an object, has to be retractable into the barrel 2. Regarding this requirement the locking members v1 and locking members v2 need to be unlocked.

Unlocking does not take place until just before or after coupling the plunger 1 to the closing-off device 3. For that purpose the first coupling means k1 and second coupling means k2 for coupling the plunger 1 to the closing-off device 3 are also adapted for unlocking the locking of the first locking members v1 to the second locking members v2.

FIGS. 2-5 show an embodiment wherein the second coupling means k2 have been arranged on the structure on which the first locking members v1 of the closing-off device 3 have also been arranged.

FIG. 2 shows the plunger 1 approaching the end of the maximum penetration, but wherein it is not yet in contact with the lock 33 that is resiliently connected to the closing-off device 3.

The lock 33 is provided with the coupling means k2 which in this embodiment are equipped with protruding barbs 34.

The first end 61 of the plunger 1 is provided with coupling means k1 which in this embodiment are equipped with protruding rigid barbs 12 for cooperation with the coupling barbs 34 on the resilient lock 33.

FIG. 3 shows a further penetration of the plunger 1 wherein the rigid barbs 12 have bent the coupling barbs 34 of the closing-off device 3 to the inside, wherein the lock 33 is pre-biased to a maximum in this direction. Simultaneously the locking barbs 35 will have been bent to the inside to such an extent that the locking between the locking members v1 and the locking members v2 is unlocked, wherein a possibility to move is realised for the closing-off device 3 in the direction of the second end 52 of the barrel 2.

Figure 4:
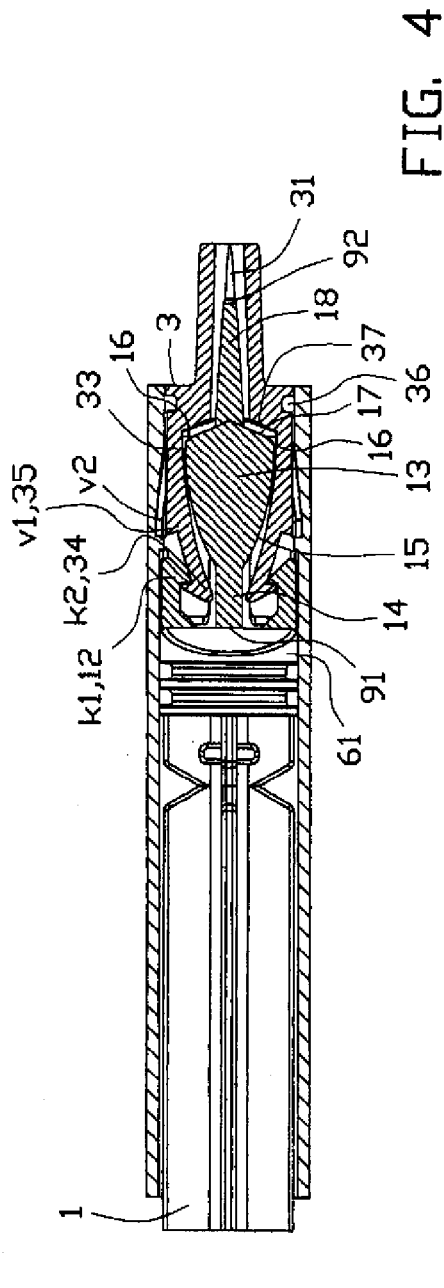
FIG. 4 shows a cross-section of the hypodermic syringe of FIG. 1 in which the closing-off device is coupled to the plunger.

FIG. 4 shows a further penetration of plunger 1 wherein the rigid barbs 12 on the first end 61 of the plunger 1 have penetrated so far into the lock 33 that the coupling barbs 34 of the closing-off device 3 have slightly flipped back again. The coupling barbs 34 engage onto the rigid barbs 12, as a result of which the plunger 1 and the closing-off device 3 are connected for together being able to slide in the direction of the second end 52 of the barrel 2.

Figure 5:
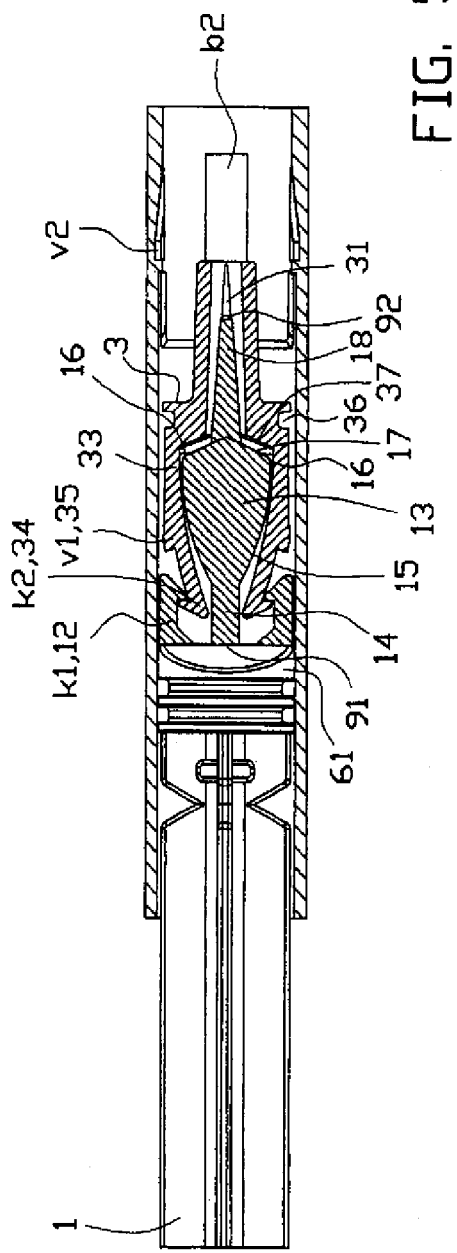
FIG. 5 shows a cross-section of the hypodermic syringe of FIG. 1 in which the assembly of the closing-off device and the plunger has slightly been retracted into the barrel.

FIG. 5 shows that due to this connection the assembly of plunger 1 and closing-off device 3 is slightly retracted in the direction of the second end 52 of the barrel 2.

FIGS. 2-5 also show the circumferential groove 36 for placing a sealing ring (not shown) at the first end 51 of the barrel 2. Said sealing ring for instance ensures that fluid cannot leak away past the closing-off device.

FIGS. 2-5 also show the shape of the first end 61 of the plunger 1. At said end not only the rigid barbs 12 are attached, so is the first end 91 of the filler body 13.

In a top view of the substantially flat filler body 13 it comprises from its first end 91 an end stem 14, a first contour 15 increasing in diameter towards its ultimate tip 16 which in the closing-off device 3 abuts an edge of the through-opening 31. Due to penetration of the plunger 1 with filler body 13 in the closing-off device 3, particularly in the recess extending over the full width of the closing-off device 3 and bounded on either side by the flexible legs of the locks 33 and in the through-opening 31, residual volume is effectively limited.

Further towards the second end 92 of the filler body 13, which end faces away from the first end 91, it comprises a second contour 17. Contour 17 is adapted for in the condition of maximum penetration of the plunger 1 having the filler body 13 abut contour 37 of the through-opening 31 at a minimum distance therefrom for limiting the residual volume.

Even further towards the second end 92 of the filler body 13 there is a tapering pin 18 which displaces the last residual volume situated at the location of the nozzle 32 in the through-opening 31 of the closing-off device.

FIG. 1 shows a view in perspective of the filler body 13. The filler body 13 is designed flat due to the shape of the closing-off device 3, of which the through-opening 31 at the end of the closing-off device 3 that faces away from the nozzle 32 is substantially flat rectangular.

The height of the through-opening 31 in the closing-off device 3 substantially corresponds with the distance between the ultimate points 16 situated at a distance on either side of the centre line of the barrel 2.

The width of the through-opening 31 in the closing-off device 3 substantially corresponds with the width of the flat filler means 13.

FIG. 2 shows a condition of the plunger 1 wherein the plunger is indeed close to a coupling to the closing-off device 3, but wherein the plunger 1 can still be individually retracted into the barrel 2. Said condition may correspond with the condition in which fluid can be sucked into the barrel 2 by sliding the plunger 1 in the direction of the second end 52 of the barrel 2 whereas the outer end of the needle device 4 is inserted in the fluid.

In order to suck up fluid, the plunger 1 should extend into the barrel to such a degree that the plunger 1 is just not yet coupled to the closing-off device 3. In order to prevent that in this action the plunger 1 is accidentally pushed further in the direction of the first end 51 of the barrel, as a result of which the plunger 1 would couple to the closing-off device 3, the plunger 1 is provided with a stop mechanism 7 near the second end 62 of the plunger 1.

Figure 6:
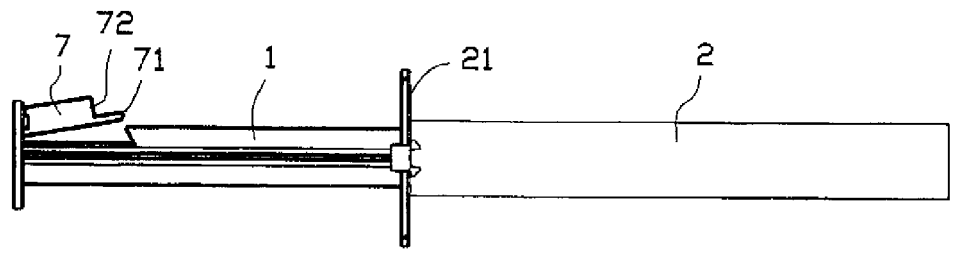
FIG. 6 shows a side view of the barrel in which the protruding plunger is situated, wherein the stop mechanism is in a first position.
Figure 7:
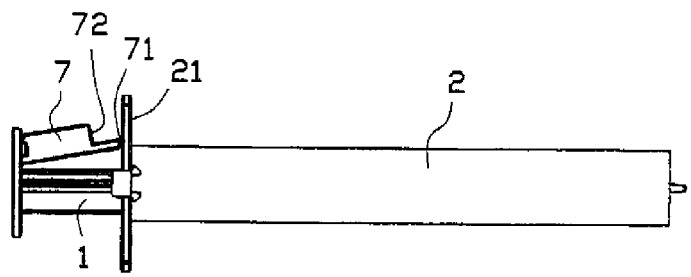
FIG. 7 shows a side view of the barrel in which the inserted plunger is situated, wherein the stop mechanism is in a first position.

FIG. 6 shows the stop mechanism 7 connected to the plunger 1, which mechanism is in a first condition. In said condition the distance the plunger 1 is able to move in the barrel 2 in the direction of the first end 51 of the barrel 2 is limited because the end 71 of the stop mechanism 7 checks the flange 21 (see FIG. 7). The movement is thus limited to such an extent that the plunger 1 cannot couple itself to the closing-off device 3 (see FIG. 2). Taking this condition as starting point, fluid can be sucked up.

Figure 8:
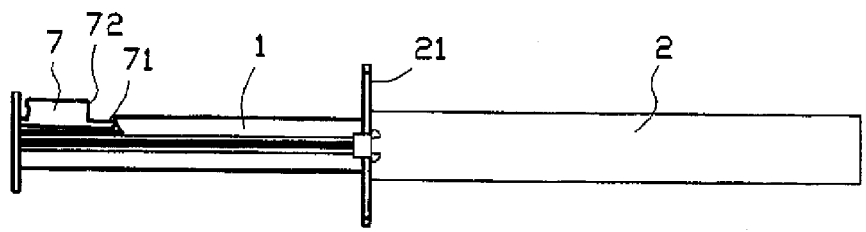
FIG. 8 shows a side view of the barrel in which the protruding plunger is situated, wherein the stop mechanism is in a second position.
Figure 9:
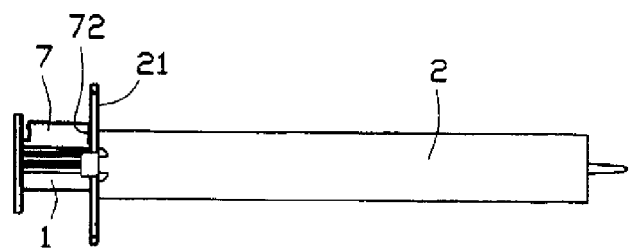
FIG. 9 shows a side view of the barrel in which the inserted plunger is situated, wherein the stop mechanism is in a second position.

FIG. 8 shows the stop mechanism 7 placed on the plunger, which mechanism is in a second condition. In this condition the distance the plunger 1 is able to move in the barrel 2 in the direction of the first end 51 of the barrel 2 is limited because the end 72 of the stop mechanism 7 checks the flange 21 (see FIG. 9). When the plunger 1 actually checks the flange the largest possible volume has been displaced and the plunger 1 has coupled itself to the closing-off device 3 (see FIG. 4). Taking this condition as starting point, the assembly of plunger 1 and the closing-off device 3 can be retracted into the barrel (see FIG. 5).

Figure 10A:
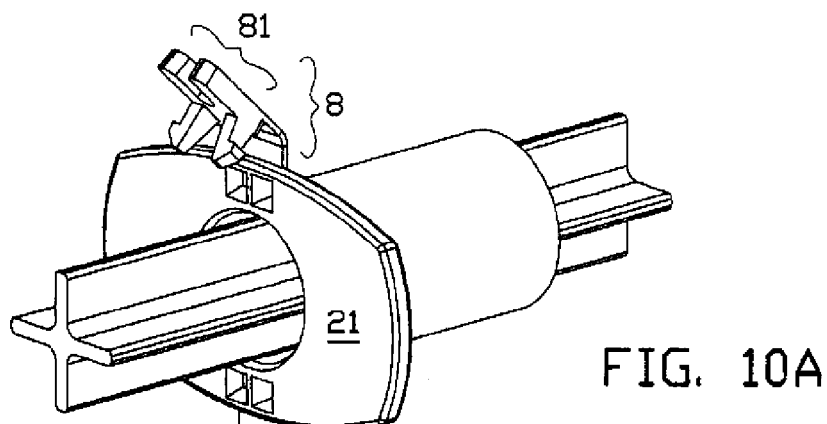
FIG. 10A shows a view in perspective wherein the guiding devices are not connected to the barrel with connecting means.

FIG. 10A shows the guiding devices 8 which with a first end thereof are flexibly connected to the flange 21. The second end facing away from the first end of the guiding device 8 comprises loose ends 81 which form the guide. In one embodiment the shape may comprise a forked structure 82.

Figure 10B:
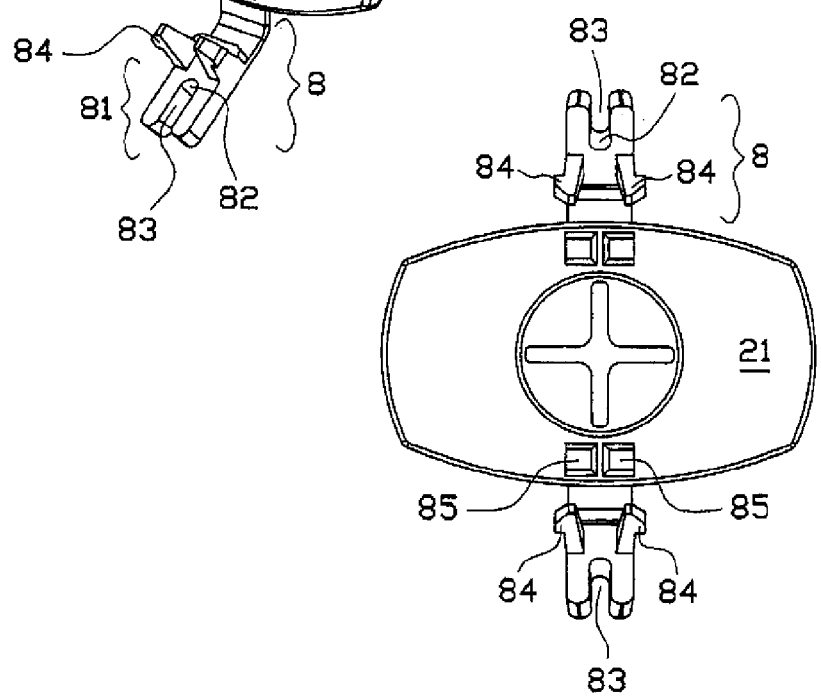
FIG. 10B shows a front view wherein the guiding devices are not connected to the barrel with connecting means.
Figure 11:
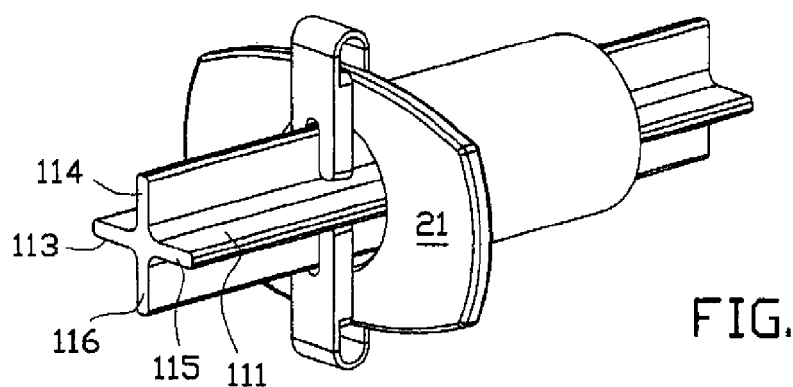
FIG. 11 shows a view in perspective wherein the guiding devices are indeed connected to the barrel with connecting means.

FIG. 10B shows a forked slot 83 of the forked structure 82 that is adapted for guiding one of the ribs 113-116 of the plunger 1 (see FIG. 11).

For such a guiding of the plunger 1 the loose ends 81 of the guiding devices 8 need to be brought into a defined position, wherein the desired rib 114, 116 of the plunger is placed in the forked slot 83.

In order to achieve this, the guiding device's 8 comprise first connecting means, wherein second connecting means cooperating therewith have for instance been arranged at the flange 21 of the barrel 2. The first and second connecting means are adapted for a mutual connection between the loose end 81 and the flange 21.

In the exemplary embodiment the guiding devices 8 comprise first connecting means barbs 84 that hitch to the clamping holes 85 arranged in the flange 21. Once the barbs 84 have been pushed through the clamping holes 85, a connection between them has been created.

In one embodiment two guiding devices 8 are used to guide two of the ribs 113-116 of the plunger 1. As the end of the closing-off device 3 facing away from the nozzle and the part of the filler means 13 of the plunger 1 which connects to the closing-off device do not have a cylindrical design, the plunger 1 should be oriented correctly in order to let the filler means 13 of the plunger 1 enter the closing-off device 3 correctly. The two guiding devices 8 are adapted for defining the correct position of the plunger 1. A correct orientation between the plunger 1 and closing-off device 3 is also necessary so that the coupling means k1 and k2 are able to couple correctly.

In addition to the functions of the guiding devices 8 described above, namely adequately guiding the plunger 1 and correctly orienting the plunger 1 in the barrel 2, the guiding device 8 has a third function. Namely bounding the movement of the plunger 1 in the direction of the second end 52 of the barrel 2. Bounding is achieved by providing the plunger 1 with movement limitation means 19 which at movement of the plunger 1 in the direction of the second end 52 of the barrel 2 finally check a part of the guiding devices 8.

Figure 12:
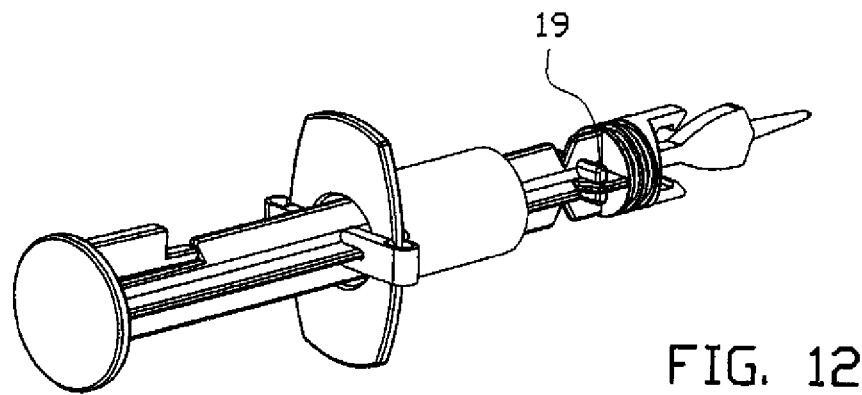
FIG. 12 shows a view in perspective of an inserted plunger, a part of the barrel and guiding devices wherein the guiding means are connected to the barrel with connecting means.

In the exemplary embodiment abutment cams 19 (see FIG. 12) have been arranged as movement limitation means.

Figure 13:
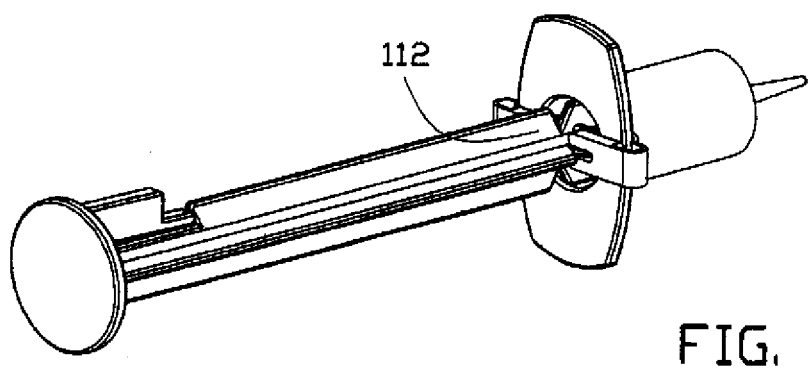
FIG. 13 shows a view in perspective of a retracted plunger, a part of the barrel and guiding devices wherein abutment cams on the plunger abut the guiding means.
Figure 14:
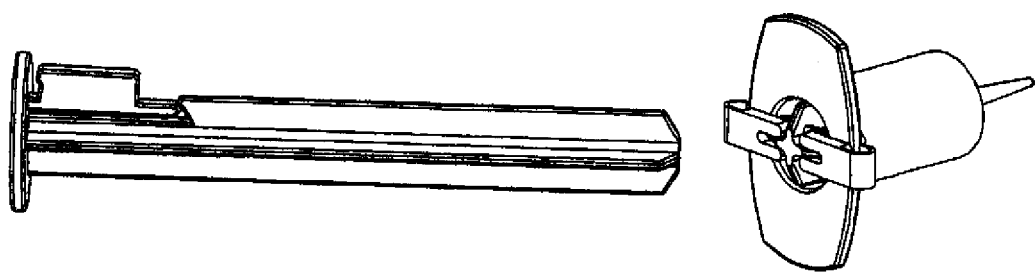
FIG. 14 shows a view in perspective of a broken plunger, a part of the barrel and guiding devices.

In this position the hypodermic syringe has a substantially long shape. It is known that processing waste is carried out more effectively when products with such a length-thickness ratio are for instance halved. FIG. 13 for that purpose shows a weakening 112 of the plunger 1 which makes it possible to reduce the length of the hypodermic syringe. The weakening 112 is situated just outside the barrel 2, near the flange 21, when the assembly comprising the plunger 1, the closing-off device 3 including the needle device 4, and the abutment cams 19 retracted in the barrel 2, abuts the guiding devices 8. In this condition the protruding part of the plunger 1 can simply be broken off from the hypodermic syringe (see FIG. 14) with little manual force.

Figure 15:
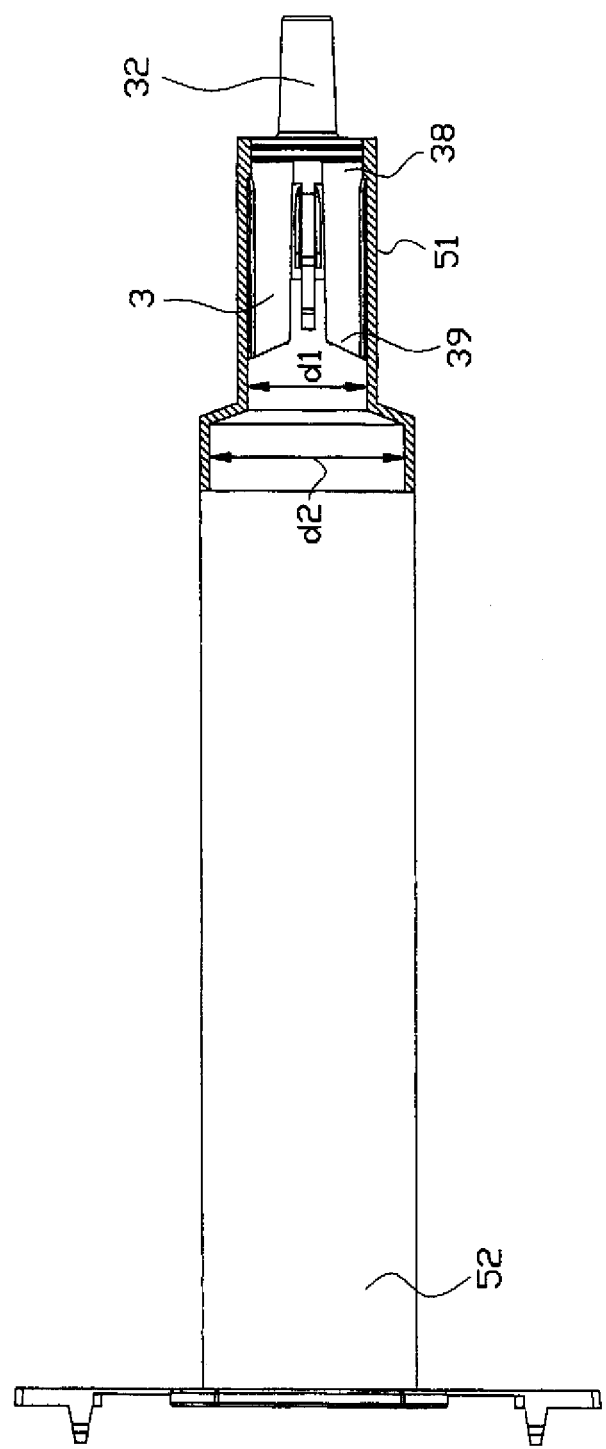
FIG. 15 shows a side view of a thickened hypodermic syringe.

FIG. 15 shows the barrel 2 and the closing-off device 3 of an exemplary embodiment of a hypodermic syringe for administering fluids of a larger volume. In this embodiment the closing-off device 3 is identical to the closing-off device 3 as described so far. In accordance therewith the barrel 2, at least at the first end 51 thereof, particularly between a first end 38 and a second end 39 of the closing-off device 3 placed in the barrel 2, is also identically designed. In order to increase the volume of the barrel 2 the inner diameter d2 of the barrel 2, at least with the exception of the position of the closing-off device 3 at the first end 51 of the barrel 2, is designed larger than the inner diameter d1 of the barrel 2. As the closing-off device 3 is identical, the characterising features of the present invention are maintained herein, wherein it is possible to place a needle of standard dimensions on the nozzle 32 that is part of the closing-off device 3 with corresponding standardised dimensions, such that after administering the fluid the needle can be stored in the barrel.

It is noted that the centre line of the widened part having diameter d2 of the barrel 2 can also be shifted parallel with respect to the centre line of the barrel 2 near the first end 51 having diameter d1.

Figure 16:
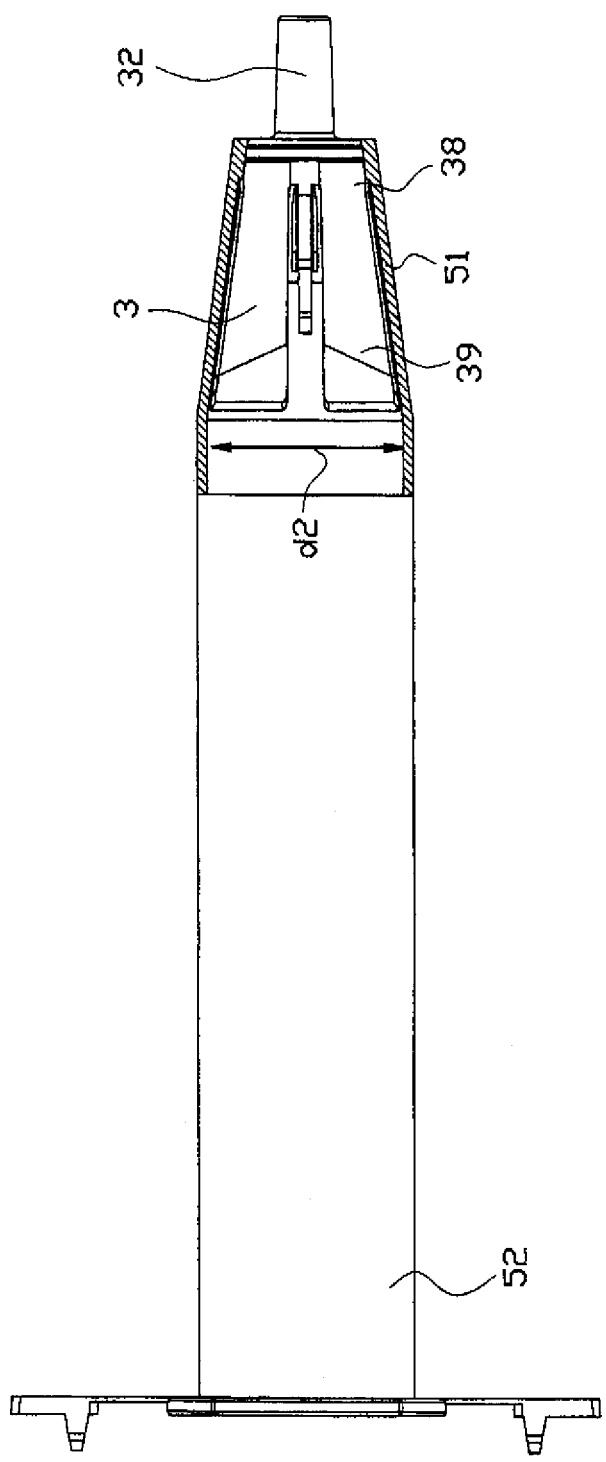
FIG. 16 shows a side view of a thickened hypodermic syringe.

FIG. 16 shows the barrel 2 and the closing-off device 3 of an embodiment of a hypodermic syringe, also for administering fluids of a larger volume. In said embodiment the closing-off device 3 differs from the closing-off device as described so far. The diameter of the closing-off device, considered from a first end 38, increases in the direction of a second end 39. In FIG. 16 there is question of a constant increase as a result of which a conical shape of the closing-off device is achieved. However, each shape of the closing-off device can be used as long as the closing-off device can be placed in the barrel such that it can be released, a requirement for retracting the needle device 4 in the barrel 2. For that purpose it is not necessary that the increase of the diameter considered from the first end 38 in the direction of the second end 39 of the closing-off device has a constant course. Locally fainter and steeper increases are also allowed.

In accordance therewith the barrel 2, at least at its first end 51, particularly between a first end 38 and a second end 39 of the closing-off device 3 placed in the barrel 2, is designed having the same contour.

The barrel 2 of the hypodermic syringe having such a different closing-off device, although not shown in the figures, may naturally also be designed having a widening of the barrel 2 as applied in the hypodermic syringe according to FIG. 15.

The different closing-off device 3 may substantially have the same characterising features of the present invention, wherein it is therefore possible to place a needle of standard dimensions on the nozzle 32 that is part of the closing-off device 3 having corresponding standard dimensions, such that after administering the fluid the needle can be stored in the barrel.

It is noted here as well that the centre line of the differing closing-off device can be shifted parallel with respect to the centre line of the barrel 2 near the first end 51 having diameter d1.

Figure 17:
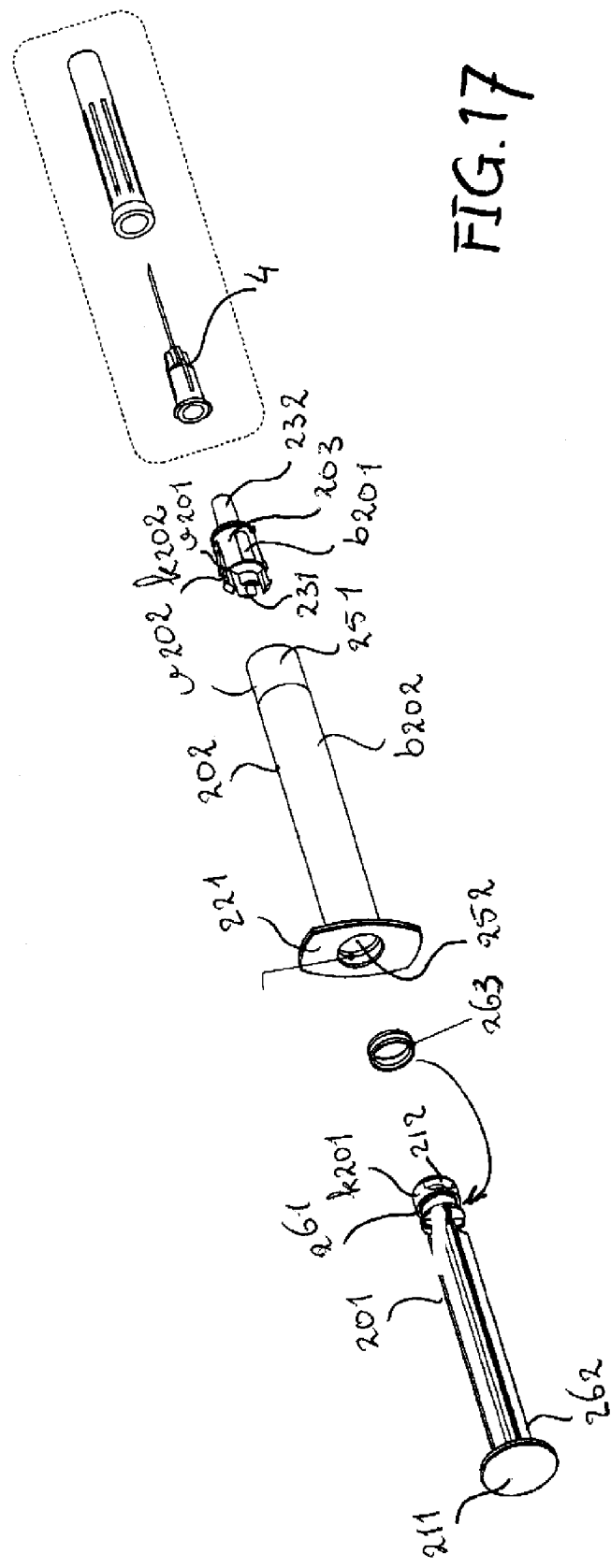
FIG. 17 shows a view in perspective of a second exemplary embodiment of a hypodermic syringe in a disassembled condition.

FIG. 17 is a disassembled view in perspective of a further exemplary embodiment of a hypodermic syringe according to the invention and shows plunger 201 (also called piston), barrel 202 (also called reservoir or housing), closing-off device 203 (also called needle mount or anchor), and needle device 204.

The barrel 202 has a substantially cylindrical inner wall, and comprises a flange 221 at a second end 252 for holding the hypodermic syringe and a first end 251 facing away from the second end of the barrel.

The closing-off device 203 is adapted for closing off the first end 251 of the barrel 202, wherein the closing-off device 203 is provided with a through-opening 231 that outwardly debouches in a nozzle 232 adapted for coupling to a needle device 4. The closing-off device 203 comprises second coupling means k202 at a side facing away from the nozzle 232.

The plunger 201 can be movably placed in the barrel 202 for pushing a fluid out of the barrel at penetration into the barrel 202, wherein the plunger 201 at least partially protrudes out of the barrel 202 at the second end 252 thereof. The first end 61 of the plunger 201 is inserted in the barrel 202. The second end 262 of the plunger facing away from the first end 261 comprises a pressing part 211. The first end 261 of the plunger comprises first coupling means k201 cooperating with the second coupling means k202, wherein first coupling means k201 and second coupling means k202 are adapted for a coupling of the plunger 201 to the closing-off device 203 in order to move the assembly of plunger 201 and closing-off device 203 in the barrel 202 in the direction of the second end 252 of the barrel 202.

Figure 19A:
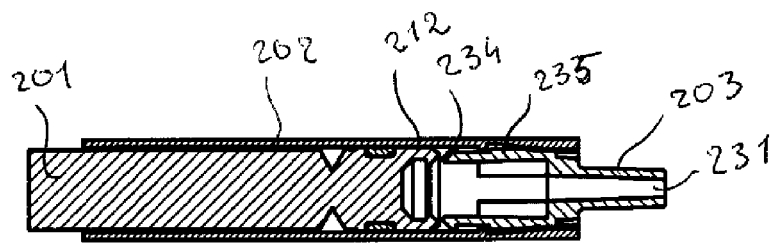
FIG. 19A shows a cross-section of the hypodermic syringe of FIG. 17 in which the plunger is situated in a position in which a coupling to the closing-off device just has not been effected yet, and wherein the sucking up of fluid could be carried out.
Figure 19B:
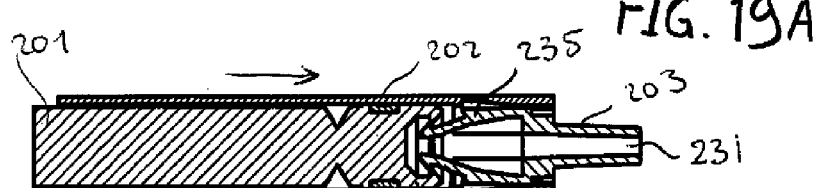
FIG. 19B shows a cross-section of the hypodermic syringe of FIG. 17 in which the closing-off device is unlocked from the barrel.
Figure 19C:
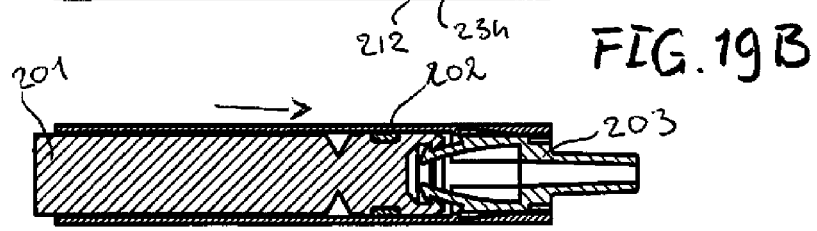
FIG. 19C shows a cross-section of the hypodermic syringe of FIG. 17 in which the closing-off device is coupled to the plunger.
Figure 19D:
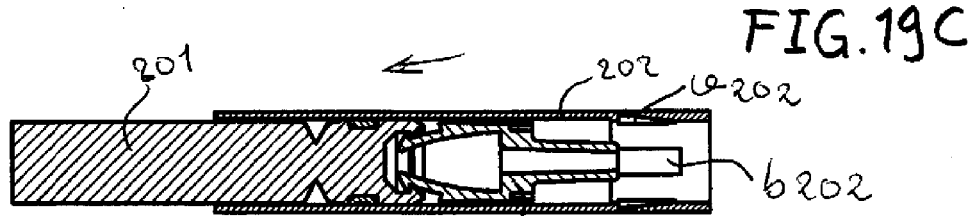
FIG. 19D shows a cross-section of the hypodermic syringe of FIG. 17 in which the assembly of the closing-off device and the plunger has been slightly retracted into the barrel.
Figure 19E:
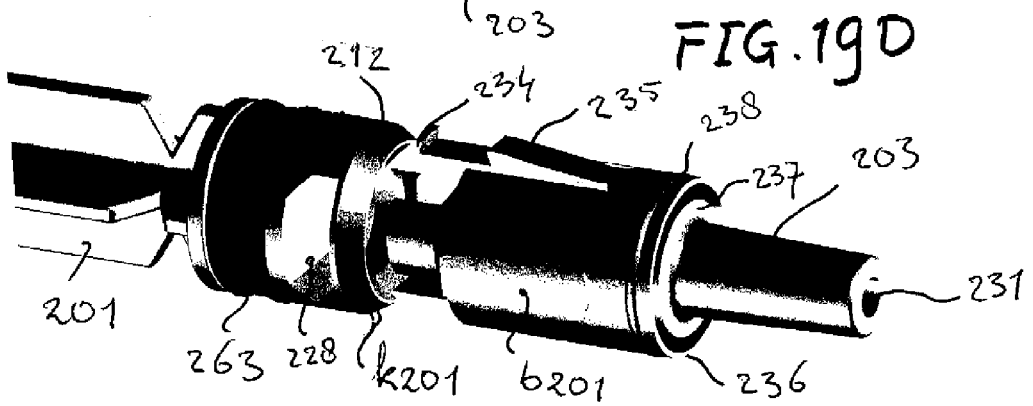
FIG. 19E shows a view in perspective of the end of the plunger and the closing-off device in uncoupled condition.

Contrary to the exemplary embodiment described above referring to FIG. 1, the first coupling means k201 are substantially circle-symmetrical, as shown in more detail in FIG. 19E. As a result the piston 201 no longer needs to be aligned with respect to the closing-off device 203 and therefore not be held rotation fixedly in the barrel 202.

FIGS. 18A and 18B show views comparable to FIGS. 1A and 1B, but then of course for the further exemplary embodiment. The side view of FIG. 18A is substantially perpendicular to the side view of FIG. 18B.

FIGS. 19A-19D show various steps in the process of coupling the plunger 201 to the closing-off device 203 and retracting the closing-off device 202 into the barrel 202.

FIG. 19A shows the plunger 201 approaching the end of the maximum penetration, but wherein it is not yet in contact with the lock 234 that is resiliently connected to the closing-off device 203.

The lock 234 is provided with the coupling means which in this embodiment are equipped with protruding barbs.

The first end 212 of the plunger 201 is provided with annular coupling means k201 which in this embodiment are equipped with a circumferential rigid snap edge, as shown in FIG. 19E, for cooperation with the coupling barbs 234 on the resilient lock.

FIG. 19B shows a further penetration of the plunger 201 wherein the snap edge 212 have bent the coupling barbs 234 of the closing-off device 203 to the inside, wherein the lock is pre-biased to a maximum in this direction. Simultaneously the locking members or barbs 235 will have been bent to the inside to such an extent that the locking between the locking members 235 and the related locking grooves is unlocked, wherein a possibility to move is realised for the closing-off device 203 in the direction of the second end of the barrel 202.

FIG. 19C shows a further penetration of the plunger 201 wherein the snap edge 212 on the first end of the plunger 201 has penetrated so far into the lock that the coupling barbs 234 of the closing-off device 203 have slightly flipped back again. The coupling barbs 234 engage onto the snap edge 212, as a result of which the plunger 201 and the closing-off device 203 are connected for together being able to slide in the direction of the second end of the barrel 202, as shown in FIG. 19D.

Furthermore the part of the closing-off device 203 placed in the barrel of this embodiment, near the end of the barrel 202 is provided with a circumferential lip or rib 238 extending radially outward, wherein the lip 238 is integrally formed with the closing-off device. The lip 238 is placed on a circumferential wall 236 of the closing-off device 203, which wall is radially spaced apart from the central part 237 of the closing-off device 203. As a result the wall 236 can be manufactured such that it runs slightly to the outside in radial direction, so that the lip 238 when the closing-off device 203 is placed in the barrel 203 as shown in FIGS. 18C and 18D, ensures an adequate sealing between the closing-off device 203 and the inner wall of the barrel 202 without an extra sealing element being necessary for that purpose.

The movement of the plunger 201 in the direction of the second end 252 of the barrel 202 is bounded. Bounding is achieved by providing the barrel 202 with an abutment ridge 219 near the second end 252 which ridge at the movement of the plunger 201 in the direction of the second end 252 of the barrel 202 will finally block the passage of the plunger 201. In the exemplary embodiment the abutment ridge 219 (see FIG. 20A) is arranged inside the barrel 202 near the second end 252 thereof.

Figure 20A:
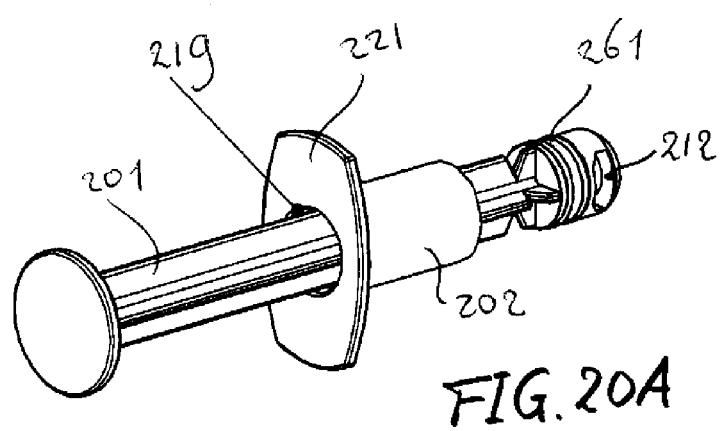
FIG. 20A shows a view in perspective of an inserted plunger, a part of the barrel and guiding devices wherein the guiding means are connected to the barrel with connecting means.
Figure 20B:
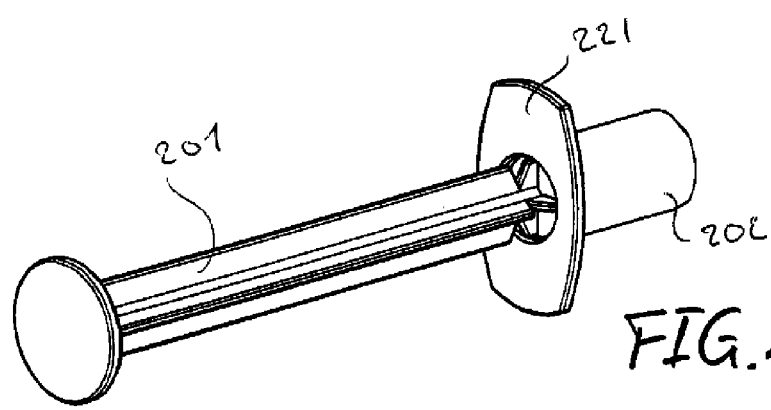
FIG. 20B shows a view in perspective of a retracted plunger, a part of the barrel and guiding devices wherein abutment cams on the plunger abut the guiding means.
Figure 20C:
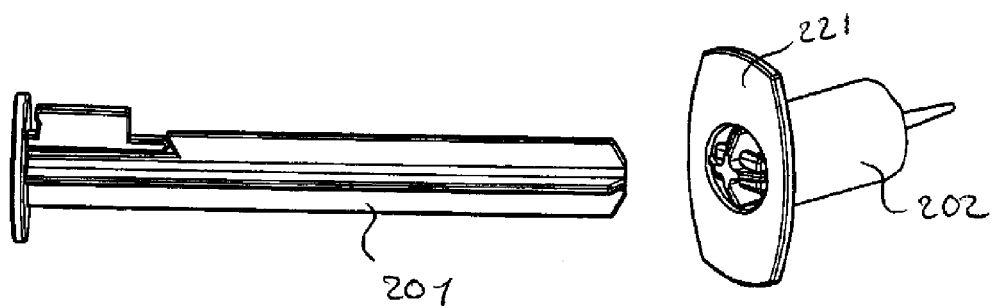
FIG. 20C shows a view in perspective of a broken plunger, a part of the barrel and guiding devices.
Figure 21:
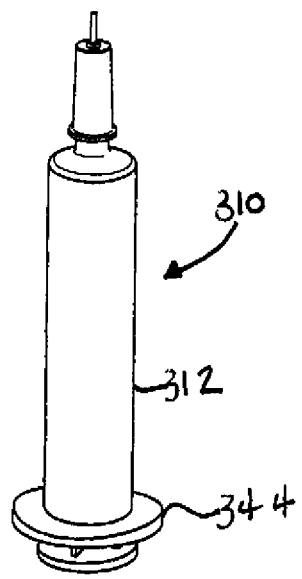
FIG. 21 shows a view in perspective of a third exemplary embodiment of hypodermic syringe comprising the hypodermic needle assembly detachably placed at the distal end of a barrel with a plunger movably placed in the barrel.

FIG. 20B shows a weakening of plunger 201 which makes it possible to reduce the length of the hypodermic syringe. When the assembly comprising the plunger 201, the closing-off device 203 including the needle device 204 is retracted into the barrel 202, the weakening abuts the abutment ridge 219. In this condition the protruding part of the plunger 201 can simply be broken off from the hypodermic syringe (see FIG. 20C) using little manual force.

It is noted that the front side of the plunger 201 may be provided with a rubber sealing 263 which can be placed on a circumferential groove 261 arranged for that purpose on the plunger.

Furthermore the front side of the plunger 201 with the snap edge 212 is provided with an opening extending sideward, as shown in FIG. 19E, through which during the manufacturing of the plunger 201 in an injection moulding process a core is passed for shaping the space behind the snap edge 212, into which the coupling barbs 234 engage.

A further exemplary embodiment is shown in FIGS. 21-31. In this exemplary embodiment the needle mount is at the outer side on the nozzle 313 of a hypodermic syringe which is in general is referred to by reference number 310.

Figure 24:
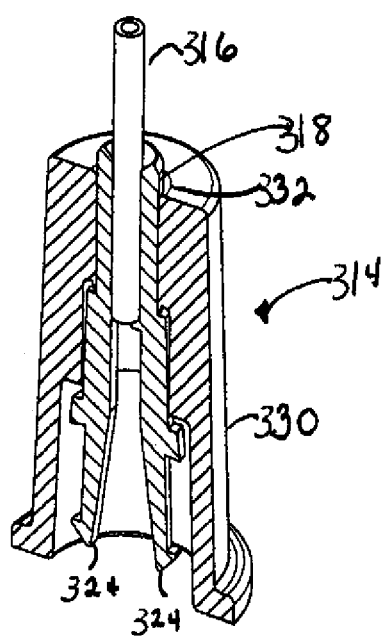
FIG. 24 shows a view in cross-section of the hypodermic needle assembly of FIG. 23, with an anchor detachably placed in a hub and a hypodermic needle connected to the anchor.

The syringe 310 comprises a cylindrical barrel 312 having a conical distal end portion 313 for detachable connection to a needle assembly 314. The needle assembly 314 comprises a needle 316 that is fixedly placed at an anchor 318 as shown in FIG. 24. The anchor 318 is adapted for coupling to a piston or plunger 320 that is movably placed in the barrel 312, wherein the needle 316 is pulled into the barrel 312 by the anchor 318 at retraction of the plunger 320 in proximal direction out of the barrel 312.

The coupling mechanism comprises the anchor 318 with two or more flexible legs 322 that end in proximal direction with outwardly facing snap elements 324 that are able to engage a snap edge 326 in a distal end 329 of the plunger 320 for forming a snap connection.

Figure 23:
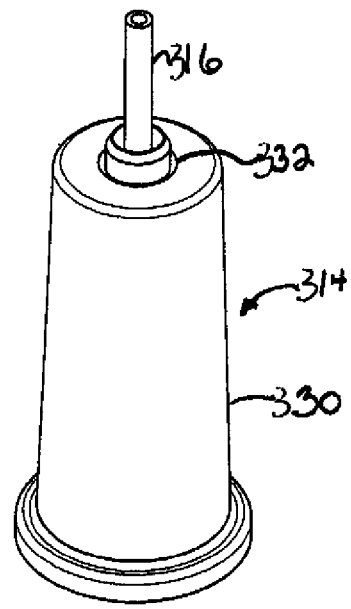
FIG. 23 shows a view in perspective of a hypodermic needle assembly according to the invention.

The hypodermic syringe 310 enables the user to administer injections in a safe and accurate manner, wherein the risk of needle prick injuries is strongly reduced. As shown in FIGS. 23 and 24 the needle assembly 314 comprises a cap 330 that can be pushed against the conical end 313 of the barrel for a friction defining and detachable connection therewith. The anchor 318 is detachably and coaxially mounted in the cap, and the needle 316 is fixedly connected to the anchor 318 by means of a screwed connection. In the known manner the distal end of the needle is provided with a sharp penetrative part (not shown) for sticking the needle into the body.

Figure 25:
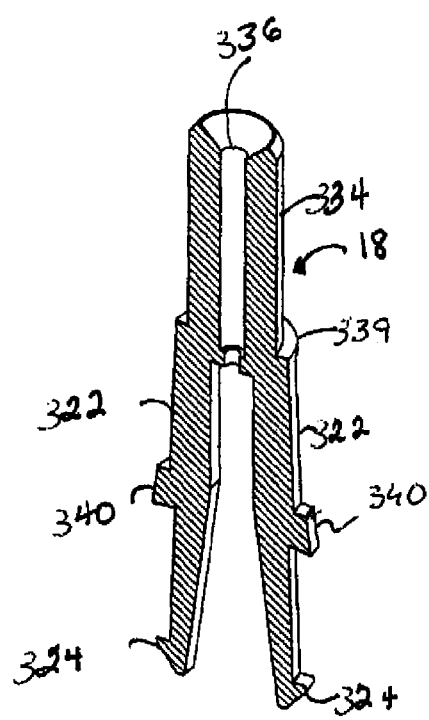
FIG. 25 shows a view in cross-section of the anchor of FIG. 24, having a substantially cylindrical distal part and a number of flexible legs ending in outwardly oriented snap elements and comprising stop means.

As shown in FIGS. 23 and 24 the cap 330 comprises a longitudinal passage 332 with which the cap can be placed around a distal part of the anchor in a snugly fitting manner. The cap defines a sealing lip 38 which substantially prevents that fluid leaks between the anchor 318 and the cap 330. As shown in FIG. 25 the anchor 318 comprises a substantially cylindrical distal end part 3334 having a longitudinal passage 336 through which the needle 316 is attached, and a proximal part that is defined by a number of flexible legs 322. The diameter of the passage 336 in the anchor 318 corresponds with the diameter of the needle which is screwed into it to attach the needle substantially without play. Anchor passages can thus be designed for making the placement therein of needles of different diameters possible.

Figure 26:
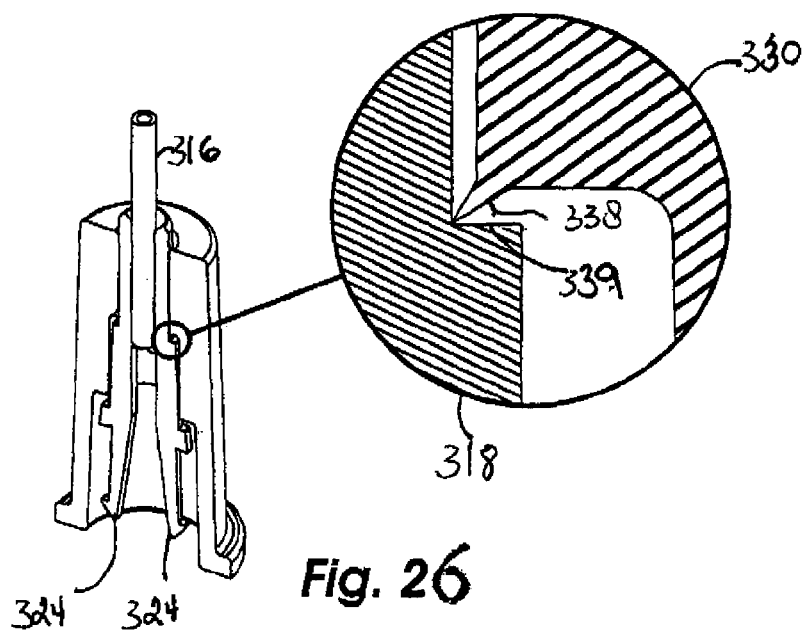
FIG. 26 shows a view comparable to FIG. 24, wherein the enlarged encircled part shows a sealing lip defined by the hub and the anchor.

As shown in FIGS. 25 and 26 the anchor 318 extends outward from the substantially cylindrical part of the anchor for defining a radial edge 339 before extending further in proximal direction to the number of flexible legs. The number of flexible legs 322 end in outwardly oriented snap elements 324 and comprise outwardly oriented cams 340, which approximately halfway the flexible legs.

As shown in FIGS. 27A-27D the outwardly oriented cams 340 have been placed in the cap between the distal end of the barrel and the substantially cylindrical part of the anchor until the anchor and needle are retracted.

During a forward movement of the plunger, the radial edge 339 of the anchor will be blocked by a sealing lip 338 substantially to prevent that the needle and anchor assembly moves out of the barrel.

FIGS. 28-30B show that the plunger 320 has a substantially cylindrical end 329 having a through-opening 328 in one side thereof and an inwardly oriented supply funnel 333 at the end for guiding the number of flexible legs of the anchor in the plunger. A substantially circular opening 335 at the bottom of a narrower part of the supply funnel 333 defines a snap edge 326 for coupling to the snap elements 324 of the anchor.

The through-opening 328 in the side of the cylindrical end 329 has the same function as the through-opening in the side of the cylindrical end k201 of the plunger of the second exemplary embodiment, as shown in FIGS. 17 and 20A. Due to said opening it is possible to integrally manufacture the plunger with a circumferential snap edge 326 in an injection moulding process.

Figure 22:
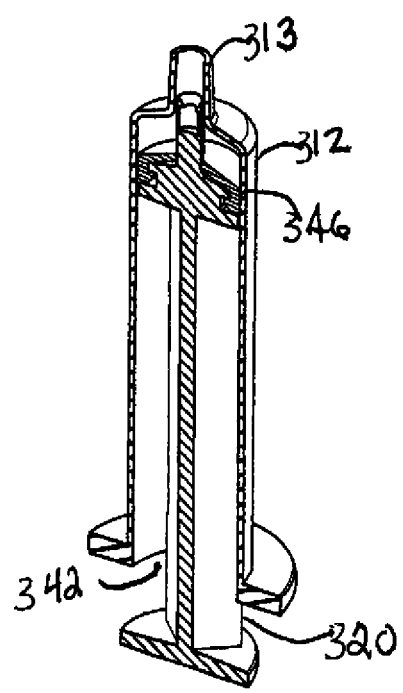
FIG. 22 shows a view in cross-section of the barrel and plunger of FIG. 21.

The substantially cylindrical distal end 329 of the plunger 320 is placed in the distal end of the barrel 313 when the plunger 320 has been placed in its distal position as shown in FIG. 22. A plunger sealing 346 substantially prevents leakage of the syringe. A medicament or the like (not shown) to be injected is placed in the barrel 312 between the sealing of the plunger and the distal end of the barrel.

When used, a suction needle (not shown) is placed on the syringe 310 by placing a conventional needle on the nozzle. The suction needle can be placed in the fluid to be injected and the fluid to be injected can be drawn into the barrel by retracting the plunger 320. It is noted here that in the first and second exemplary embodiment such a suction needle is not necessary and that for fully filling the syringe and injecting the fluid the same conventional needle can be used.

Figure 27A:
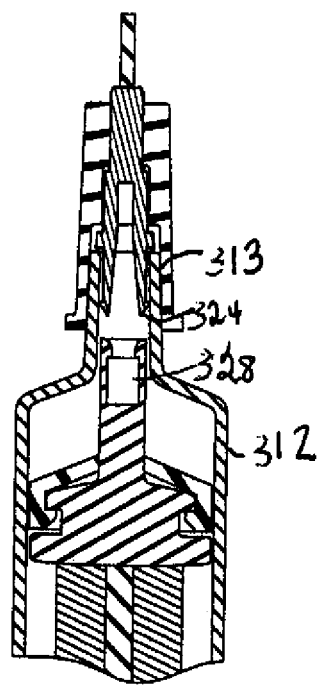
FIG. 27A shows a view in partial cross-section of the syringe of FIG. 21, with a distal end of the plunger inside a part of the barrel.
Figure 27B:
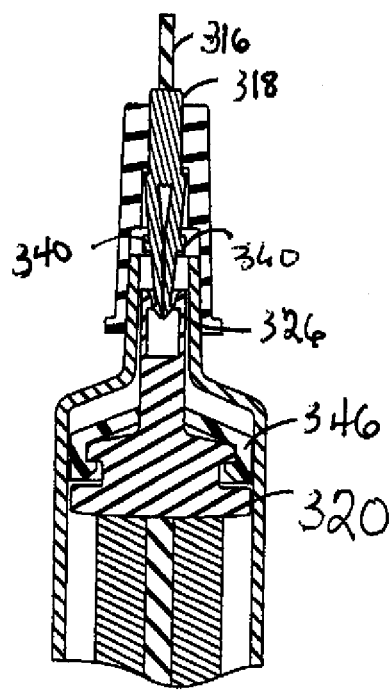
FIG. 27B shows a view comparable to FIG. 27A, with a more distal position of the plunger.
Figure 27C:
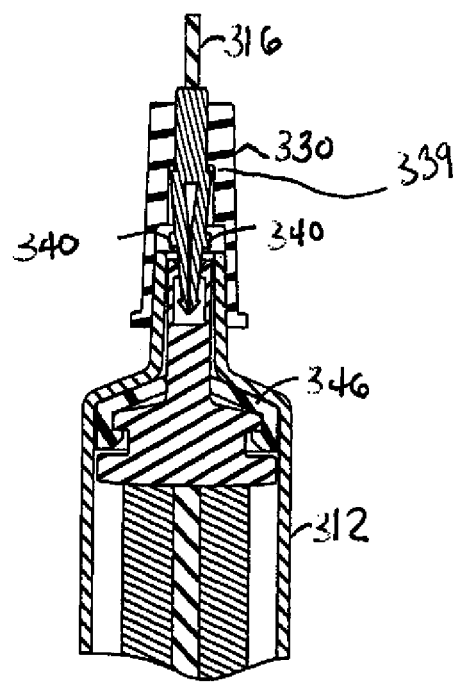
FIG. 27C shows a view comparable to FIGS. 27A and 27B, with the distal end of the plunger at a fully distal position inside the barrel with the flexible legs of the anchor inside the plunger.
Figure 27D:
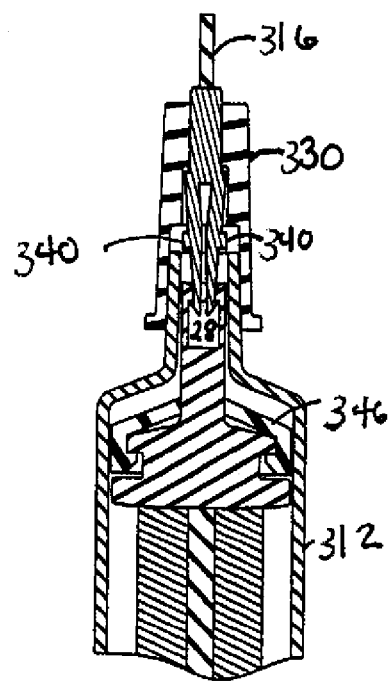
FIG. 27D shows a view comparable to FIGS. 27A-C, with the outwardly oriented snap elements of the plunger.

Subsequently the conventional needle is removed and the needle assembly 314 as shown in FIGS. 23 and 24 is placed on the nozzle of the barrel 313. After the medication has been administered, the continuous movement of the plunger ensures that the distal end 328 is moved in the direction of the snap elements 324 as shown in FIG. 27A. When pushing the plunger further the flexible legs 340 of the anchor are bent inwards as shown in FIG. 27B, in order to be received in the distal end 326 of the plunger. When the plunger has been fully pushed into the barrel, as shown in FIG. 27C, the snap elements 324 are placed past the snap edge 326, as a result of which the flexible legs are able to slightly relax again so that the snap elements 324 are able to engage under the snap edge 326, as shown in FIG. 27D. In this way the anchor is actively and effectively coupled to the plunger 320.

Figure 27E:
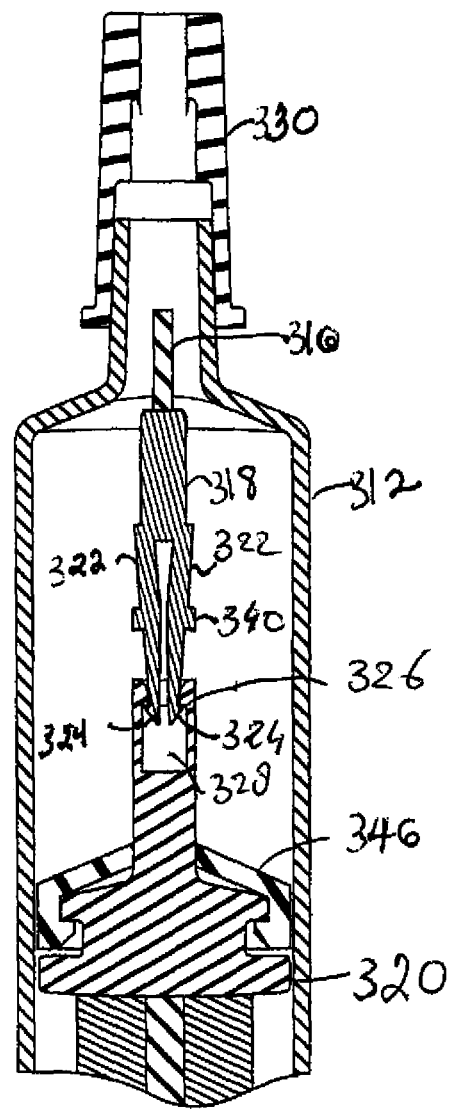
FIG. 27E shows a view comparable to FIGS. 27A-D, with a full retraction of the plunger, the anchor and the needle pulled inside the barrel.
Figure 28:
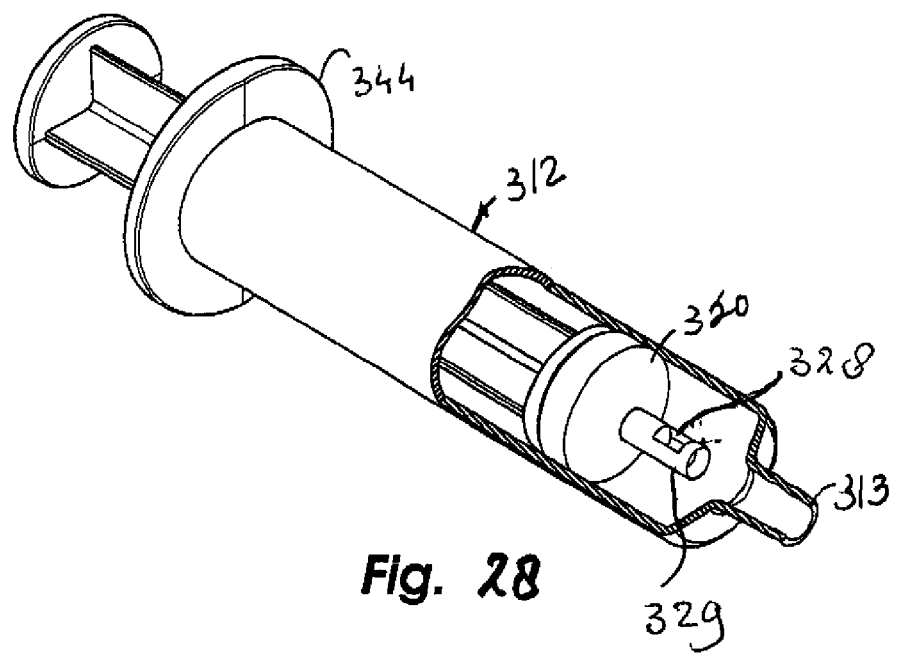
FIG. 28 shows a view in perspective of the syringe barrel of FIG. 22, with a part of the barrel cut-away in order to disclose the distal end of the plunger.
Figure 29:
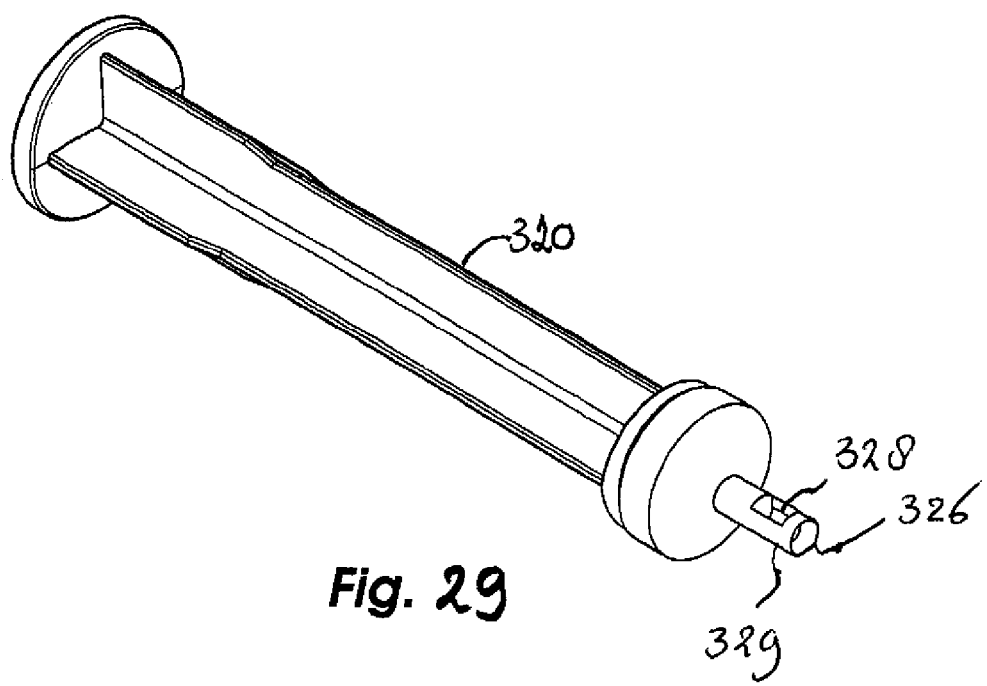
FIG. 29 shows a view in perspective of the plunger.
Figure 30A:
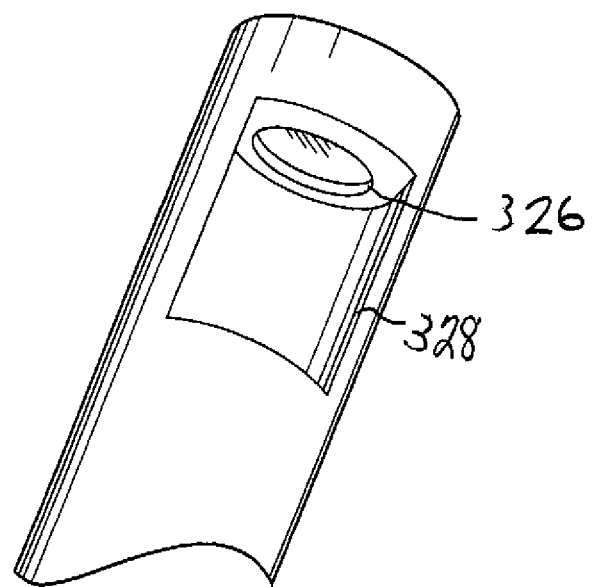
FIG. 30A shows an enlarged partial view in perspective of the distal end of the plunger, including the snap edge of the plunger.
Figure 30B:
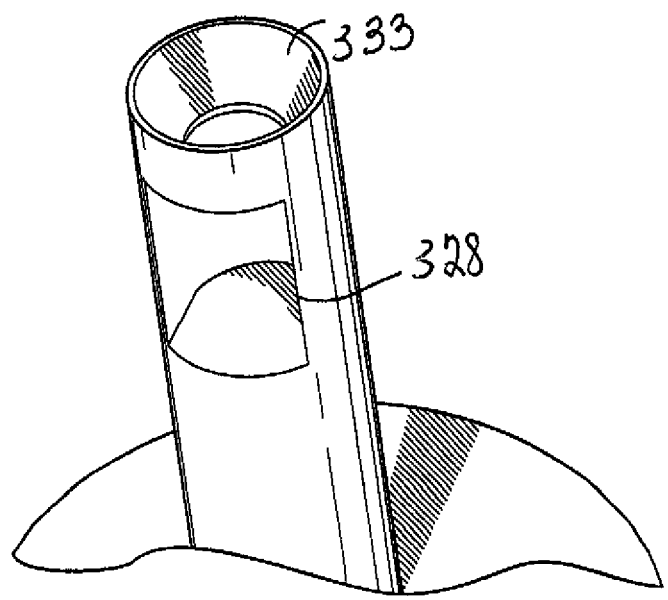
FIG. 30B shows a further enlarged partial view in perspective of the distal end of the plunger.

The cams 340 prevent a movement of the anchor and the needle to the inside of the barrel, for instance during inserting the needle into a patient during the injection. As shown in FIG. 27D said cams 340 have been moved to the inside when the anchor is coupled to the plunger. As a result it will be possible to retract the anchor and the needle into the barrel, as shown in FIG. 27E. In this way the needle can be stored within the barrel of a hypodermic syringe for safe transport and discharge of the hypodermic syringe.

Each of the above-mentioned steps is also shown in FIG. 31.

The above description is included to illustrate the operation of preferred embodiments of the invention and not to limit the scope of the invention. Starting from the above explanation many variations that fall within the spirit and scope of the present invention will be evident to an expert.

The invention claimed is:

1. Hypodermic syringe comprising:
   a barrel with an inner wall thereof defining a reservoir, said barrel comprising a first section near a first end of the barrel and a second section near a second end of the barrel,
   a closing-off device, placed in the first section of the barrel, for closing off the first end of the barrel, wherein the closing-off device is provided with a through-opening outwardly debouching in a nozzle adapted for a coupling to a needle device,
   a plunger, slidably placed in the second section of the barrel, for pushing a fluid out of the barrel at penetration into the barrel, wherein the plunger at least partially protrudes out of the barrel at the second end thereof, and wherein a first end of the plunger is inserted in the barrel and comprises first coupling members,
   wherein the closing-off device is adapted to be moveable relative to said barrel and comprises a circumferential wall that sealingly abuts the inner wall of the first section of the barrel,
   wherein the closing-off device at the side facing away from the nozzle is provided with a recess extending along a centre line of the closing-off device and over the full width of the closing-off device, which recess in the direction of the nozzle merges into the through-opening, wherein in the recess two diametrically opposite flexible locking members are placed that extend in the longitudinal direction of the recess and towards the circumferential wall of said closing-off device, which locking members by engaging into diametrically placed locking grooves in the inner wall of said barrel lock the closing-off device against a movement in the direction from the first end to the second end of the barrel, wherein the locking members at or near their end facing away from the nozzle comprise second coupling members for coupling to the first coupling members, and wherein the closing-off device at the side facing away from the nozzle, at a circumferential part of the closing-off device that is situated outside of the recess, is provided with two diametrically opposite blocking members that extend substantially parallel to the centre line of the closing-off device and extend radially outward, which blocking members by engaging into diametrically placed blocking grooves in the inner wall of the barrel lock the closing-off device against a movement in the direction from the second end to the first end of the barrel.

2. Hypodermic syringe according to claim 1, wherein the locking members and the locking grooves form a form closure in the direction towards the second end, and the blocking members and the blocking grooves form a form closure in the direction towards the first end.

3. Hypodermic syringe according to claim 1, wherein the locking members and the locking grooves form a force closure in the direction towards the first end.

4. Hypodermic syringe according to claim 1, wherein the first section of the barrel at a side thereof that faces away from the first end is bounded by a circumferential edge, wherein the first section has a smaller inner diameter than a part of the barrel situated beyond the edge/ wherein the blocking groove is formed in said first section and debouches in the edge.

5. Hypodermic syringe according to claim 1, wherein the locking grooves and the blocking grooves are placed substantially at a same circumference at the inner side of the barrel.

6. Hypodermic syringe according to claim 1, wherein a first plane through the centre lines of the blocking grooves is placed substantially perpendicular to the second plane through the centre lines of the locking grooves.

7. Hypodermic syringe according to claim 6, wherein an intersecting line between said first and second plane coincides with the centre line of the hypodermic syringe.

8. Hypodermic syringe according to claim 1, wherein the first and second coupling members are adapted for unlocking the locking of the locking members with the locking grooves.

9. Hypodermic syringe according to claim 1, wherein the inner wall of the first section of the barrel is substantially cylindrical or has an increasing diameter course in a direction from the first end towards the second end of the barrel.

10. Hypodermic syringe according to claim 1, wherein the dimensions of the nozzle are adapted for a coupling to a needle or needle device suitable or intended for standard hypodermic syringes, particularly hypodermic syringes without retraction device.

11. Hypodermic syringe according to claim 1, wherein the closing-off device comprises a first end near the first end of the barrel, wherein the diameter of said first end exceeds a diameter of the standard needle device.

12. Hypodermic syringe according to claim 1, wherein the diameter of the closing-off device at the first end exceeds 6 mm.

13. Hypodermic syringe according to claim 1, wherein an inner diameter of the second section of the barrel, comprising a substantially cylindrical inner wall, exceeds or equals an outer diameter of the closing-off device.

14. Hypodermic syringe according to claim 1, wherein the shape of the end of the plunger that is inserted in the barrel in the condition of deepest penetration substantially fits close to the shape of the end of the closing-off device present in the barrel.

15. Hypodermic syringe according to claim 1, wherein the plunger is provided with a filler body adapted to at least partially fill the through-opening.

16. Hypodermic syringe according to claim 1, wherein the hypodermic syringe comprises a stop mechanism adapted for blocking a movement of the plunger in the direction of the first end of the barrel, wherein the stop mechanism in a first position bounds the plunger that is to penetrate the barrel so that the first end of the plunger does not couple itself to the closing-off device, and wherein the stop mechanism in a second position allows the plunger that is to penetrate the barrel to couple to the closing-off device.

17. Hypodermic syringe according to claim 16, wherein the stop mechanism in the second position blocks the assembly comprising the plunger and the closing-off device against said assembly thrusting through in the direction of the first end of the barrel.

18. Hypodermic syringe according to claim 16, wherein the stop mechanism is arranged near the second end of the plunger.

19. Hypodermic syringe according to claim 1, wherein the barrel comprises a guiding device for guiding the plunger.

20. Hypodermic syringe according to claim 19, wherein the guiding device comprises first connecting means, and the barrel comprises second connecting means cooperating with the first connecting means, wherein the first and second connecting means are adapted for connecting the guiding device to the barrel.

21. Hypodermic syringe according to claim 1, wherein the plunger comprises a rib extending in the longitudinal direction of the plunger, and the guiding device comprises an end comprising protruding parts for at least partially embracing the rib.

22. Hypodermic syringe according to claim 1, wherein the plunger comprises movement limitation means for checking the guiding device on the barrel, which means limit movement of the plunger in the direction of the second end of the barrel.

23. Hypodermic syringe according to claim 1, wherein the plunger comprises a weakened portion for breaking and splitting the plunger, wherein the weakened portion is placed particularly near the end of the plunger that is present in the barrel.

24. Hypodermic syringe according to claim 1, wherein the second section of the barrel, comprising a substantially cylindrical inner wall, has a cross-sectional surface exceeding or equalling a cross-sectional surface of the first section of the barrel.

25. Hypodermic syringe according to claim 1, wherein the plunger is provided with a filler body adapted to at least partially fill the recess and the through-opening in the closing-off device.

26. Hypodermic syringe according to claim 1, wherein the closing-off device at an end situated near the first end of the barrel is provided with a rib which runs around the closing-off device and extends radially outward, wherein the rib is integrally formed with the closing-off device.

27. Hypodermic syringe according to claim 1, wherein, when the locking means engage the locking groove and/or the blocking means engage the blocking groove, said nozzle of said closing-off device extends out of said barrel for attaching said needle device to an outer surface of said nozzle.

28. Hypodermic syringe according to claim 1, wherein, when the locking means engage the locking groove and/or the blocking means engage the blocking groove, said nozzle is arranged for coupling said needle device thereto with said needle device and/or a needle of said needle device arranged completely outside of said barrel.

29. Hypodermic syringe according to claim 12, wherein the diameter of the closing-off device at the first end exceeds 8 mm.

* * * * *